United States Patent
Nilsson et al.

(10) Patent No.: US 11,052,062 B2
(45) Date of Patent: **\*Jul. 6, 2021**

(54) CONTROLLED RELEASE PHARMACEUTICAL COMPOSITIONS COMPRISING A FUMARIC ACID ESTER

(71) Applicant: Biogen Swiss Manufacturing GmbH, Baar (CH)

(72) Inventors: Henrik Nilsson, Dubai (AE); Bernd W. Mueller, Flintbek (DE)

(73) Assignee: Biogen Swiss Manufacturing GmbH, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/525,392

(22) Filed: Jul. 29, 2019

(65) Prior Publication Data

US 2019/0343787 A1 Nov. 14, 2019

Related U.S. Application Data

(63) Continuation of application No. 16/227,287, filed on Dec. 20, 2018, which is a continuation of application (Continued)

(30) Foreign Application Priority Data

Oct. 8, 2004 (DK) .......................... PA 2004 01546
Nov. 10, 2004 (DK) .......................... PA 2004 01736
(Continued)

(51) Int. Cl.
*A61K 31/225* (2006.01)
*A61K 9/28* (2006.01)
(Continued)

(52) U.S. Cl.
CPC .......... *A61K 31/225* (2013.01); *A61K 9/0053* (2013.01); *A61K 9/14* (2013.01);
(Continued)

(58) Field of Classification Search
CPC . A61K 9/14; A61K 9/20; A61K 9/167; A61K 9/28; A61K 9/48; A61K 9/50;
(Continued)

(56) References Cited

U.S. PATENT DOCUMENTS 2,764,609 A 9/1956 Gamrath et al.
3,078,302 A 2/1963 Franz et al.
(Continued)

FOREIGN PATENT DOCUMENTS

AU 2013203445 B2 10/2016
AU 2013203445 C1 4/2017
(Continued)

OTHER PUBLICATIONS

Altmeyer et al., 1994, "Antisoriatic effect of fumaric acid derivatives. Results of a multicenter double-blind study in 100 patients", J. Am. Acad. Dermatol., 30:977-981.
(Continued)

*Primary Examiner* — Lakshmi S Channavajjala
(74) *Attorney, Agent, or Firm* — Jones Day

(57) ABSTRACT

The present invention relates to controlled release pharmaceutical compositions comprising fumaric acid ester(s) as active substance(s). The compositions are suitable for use in the treatment of e.g. psoriasis or other hyperproliferative, inflammatory or autoimmune disorders and are designated to release the fumaric acid ester in a controlled manner so that local high concentrations of the active substance within the gastrointestinal tract upon oral administration can be avoided and, thereby, enabling a reduction in gastro-intestinal related side-effects.

8 Claims, 3 Drawing Sheets

Related U.S. Application Data

No. 15/988,628, filed on May 24, 2018, now abandoned, which is a continuation of application No. 15/728,872, filed on Oct. 10, 2017, now abandoned, which is a continuation of application No. 14/209,480, filed on Mar. 13, 2014, now abandoned, which is a continuation of application No. 11/576,871, filed as application No. PCT/DK2005/000648 on Oct. 7, 2005, now abandoned.

(60) Provisional application No. 60/691,513, filed on Jun. 16, 2005.

(30) Foreign Application Priority Data

Feb. 11, 2005 (DK) .................. PA 2005 00211
Mar. 23, 2005 (DK) .................. PA 2005 00419

(51) Int. Cl.
| | | |
|---|---|---|
| *A61K 45/06* | (2006.01) | |
| *A61K 9/20* | (2006.01) | |
| *A61K 9/48* | (2006.01) | |
| *A61K 31/215* | (2006.01) | |
| *A61K 31/22* | (2006.01) | |
| *A61K 9/50* | (2006.01) | |
| *A61K 9/14* | (2006.01) | |
| *A61K 9/16* | (2006.01) | |
| *A61K 9/00* | (2006.01) | |

(52) U.S. Cl.
CPC .............. *A61K 9/167* (2013.01); *A61K 9/20* (2013.01); *A61K 9/2013* (2013.01); *A61K 9/2027* (2013.01); *A61K 9/2031* (2013.01); *A61K 9/2054* (2013.01); *A61K 9/2077* (2013.01); *A61K 9/2081* (2013.01); *A61K 9/28* (2013.01); *A61K 9/2846* (2013.01); *A61K 9/2853* (2013.01); *A61K 9/2866* (2013.01); *A61K 9/48* (2013.01); *A61K 9/4808* (2013.01); *A61K 9/4891* (2013.01); *A61K 9/50* (2013.01); *A61K 9/5042* (2013.01); *A61K 9/5047* (2013.01); *A61K 9/5084* (2013.01); *A61K 31/215* (2013.01); *A61K 31/22* (2013.01); *A61K 45/06* (2013.01)

(58) Field of Classification Search
CPC .. A61K 9/2846; A61K 9/0053; A61K 31/225; A61K 9/2077; A61K 9/2081; A61K 9/4808
See application file for complete search history.

(56) References Cited

U.S. PATENT DOCUMENTS

| | | |
|---|---|---|
| 4,145,438 A | 3/1979 | Kingsley et al. |
| 4,302,440 A | 11/1981 | John et al. |
| 4,693,896 A | 9/1987 | Wheatley et al. |
| 4,827,022 A | 5/1989 | Makowka et al. |
| 4,851,439 A | 7/1989 | Speiser et al. |
| 4,911,917 A | 3/1990 | Kuhrts |
| 4,952,594 A | 8/1990 | Mercer |
| 4,959,389 A | 9/1990 | Speiser et al. |
| 5,023,245 A | 6/1991 | Kuhrts |
| 5,149,695 A | 9/1992 | Speiser et al. |
| 5,214,196 A | 5/1993 | Blank |
| 5,242,905 A | 9/1993 | Blank |
| 5,401,512 A | 3/1995 | Rhodes et al. |
| 5,424,332 A | 6/1995 | Speiser et al. |
| 5,451,667 A | 9/1995 | Speiser et al. |
| 5,484,610 A | 1/1996 | Bae |
| 5,589,504 A | 12/1996 | Dannenberg et al. |
| 5,681,584 A | 10/1997 | Savastano et al. |
| 5,716,625 A | 2/1998 | Hahn et al. |
| 5,804,203 A | 9/1998 | Hahn et al. |
| 5,851,556 A | 12/1998 | Breton et al. |
| 5,856,356 A | 1/1999 | Tsouderos et al. |
| 6,022,562 A | 2/2000 | Autant et al. |
| 6,139,850 A | 10/2000 | Hahn et al. |
| 6,277,882 B1 | 8/2001 | Joshi et al. |
| 6,344,676 B1 | 2/2002 | Yun et al. |
| 6,355,676 B1 | 3/2002 | Joshi et al. |
| 6,359,003 B1 | 3/2002 | Joshi et al. |
| 6,436,992 B1 | 8/2002 | Joshi et al. |
| 6,509,376 B1 * | 1/2003 | Joshi .................. A61K 9/28 514/547 |
| 6,537,584 B1 | 3/2003 | Zentner et al. |
| 6,613,800 B1 | 9/2003 | Smith |
| 6,627,214 B1 | 9/2003 | Bunick et al. |
| 6,730,693 B2 | 5/2004 | Buononato |
| 6,812,248 B2 | 11/2004 | Zhang et al. |
| 6,858,750 B2 | 2/2005 | Joshi et al. |
| 7,157,423 B2 | 1/2007 | Joshi et al. |
| 7,320,999 B2 | 1/2008 | Joshi et al. |
| 7,432,240 B2 | 10/2008 | Joshi et al. |
| 7,612,110 B2 | 11/2009 | Joshi et al. |
| 7,619,001 B2 | 11/2009 | Joshi et al. |
| 7,790,916 B2 | 9/2010 | Joshi et al. |
| 7,803,840 B2 | 9/2010 | Joshi et al. |
| 7,906,659 B2 | 3/2011 | Joshi et al. |
| 7,915,310 B2 | 3/2011 | Joshi et al. |
| 8,067,467 B2 | 11/2011 | Joshi et al. |
| 8,148,414 B2 | 4/2012 | Gangakhedkar et al. |
| 8,399,514 B2 | 3/2013 | Lukashev et al. |
| 8,524,773 B2 | 9/2013 | Joshi et al. |
| 8,906,420 B2 * | 12/2014 | Nilsson .................. A61K 9/2054 424/490 |
| 9,326,947 B1 | 5/2016 | Dyakonov et al. |
| 9,326,965 B2 | 5/2016 | Dyakonov et al. |
| 9,511,043 B2 | 12/2016 | Dyakonov et al. |
| 9,517,209 B2 | 12/2016 | Dyakonov et al. |
| 9,566,259 B1 | 2/2017 | Vaughn et al. |
| 9,636,318 B2 | 5/2017 | Vaughn et al. |
| 9,636,319 B1 | 5/2017 | Vaughn et al. |
| 9,814,691 B2 | 11/2017 | Dyakonov et al. |
| 9,814,692 B2 | 11/2017 | Vaughn et al. |
| 9,820,960 B2 | 11/2017 | Dyakonov et al. |
| 9,820,961 B2 | 11/2017 | Vaughn et al. |
| 10,098,863 B2 | 10/2018 | Vaughn et al. |
| 2002/0002306 A1 | 1/2002 | Kadowaki et al. |
| 2002/0016369 A1 | 2/2002 | Villa et al. |
| 2002/0098185 A1 | 7/2002 | Sims et al. |
| 2003/0013761 A1 | 1/2003 | Joshi et al. |
| 2003/0018072 A1 | 1/2003 | Joshi et al. |
| 2003/0152622 A1 | 8/2003 | Louie-Helm et al. |
| 2003/0180362 A1 | 9/2003 | Park et al. |
| 2003/0185915 A1 | 10/2003 | Carlo et al. |
| 2003/0219456 A1 | 11/2003 | Ok |
| 2004/0002544 A1 | 1/2004 | Makino et al. |
| 2004/0038889 A1 | 2/2004 | Joshi et al. |
| 2004/0038904 A1 | 2/2004 | Ogden |
| 2004/0054001 A1 | 3/2004 | Joshi et al. |
| 2005/0148664 A1 | 7/2005 | Joshi et al. |
| 2005/0220878 A1 | 10/2005 | Fegely et al. |
| 2005/0220909 A1 | 10/2005 | Theoharides |
| 2006/0205659 A1 | 9/2006 | Joshi et al. |
| 2007/0027076 A1 | 2/2007 | Joshi et al. |
| 2007/0071819 A1 | 3/2007 | Kesarwani et al. |
| 2007/0248662 A1 | 10/2007 | Joshi et al. |
| 2007/0248663 A1 | 10/2007 | Joshi et al. |
| 2008/0004344 A1 | 1/2008 | Nilsson et al. |
| 2008/0227847 A1 | 9/2008 | Nilsson et al. |
| 2008/0233185 A1 | 9/2008 | Joshi et al. |
| 2008/0274182 A1 | 11/2008 | Alida Boekema et al. |
| 2008/0299196 A1 | 12/2008 | Nilsson et al. |
| 2008/0300217 A1 | 12/2008 | Nilsson |
| 2009/0011986 A1 | 1/2009 | Joshi et al. |
| 2009/0018175 A1 | 1/2009 | Kanari et al. |
| 2009/0181085 A1 | 7/2009 | Joshi et al. |
| 2009/0182047 A1 | 7/2009 | Joshi et al. |
| 2009/0215145 A1 | 8/2009 | Park et al. |

(56) References Cited

U.S. PATENT DOCUMENTS

| | | |
|---|---|---|
| 2009/0304790 A1 | 12/2009 | Nilsson et al. |
| 2010/0048651 A1 | 2/2010 | Gangakhedkar et al. |
| 2010/0130607 A1 | 5/2010 | Gold |
| 2010/0144651 A1 | 6/2010 | Nilsson et al. |
| 2010/0316706 A1 | 12/2010 | Joshi et al. |
| 2010/0324327 A1 | 12/2010 | Lee |
| 2011/0112196 A1 | 5/2011 | Lukashev |
| 2011/0124615 A1 | 5/2011 | Joshi et al. |
| 2011/0293711 A1 | 12/2011 | Joshi et al. |
| 2012/0020954 A1 | 1/2012 | Achrion et al. |
| 2012/0034274 A1 | 2/2012 | Nilsson et al. |
| 2012/0034303 A1 | 2/2012 | Nilsson et al. |
| 2012/0165404 A1 | 6/2012 | Lukashev |
| 2012/0196931 A1 | 8/2012 | Lukashev et al. |
| 2013/0004526 A1 | 1/2013 | Joshi et al. |
| 2013/0216615 A1 | 8/2013 | Goldman et al. |
| 2013/0295169 A1 | 11/2013 | Goldman et al. |
| 2014/0099364 A2 | 4/2014 | Nilsson et al. |
| 2014/0199390 A1 | 7/2014 | Nilsson et al. |
| 2014/0199392 A1 | 7/2014 | Nilsson et al. |
| 2014/0199393 A1 | 7/2014 | Nilsson et al. |
| 2014/0205659 A1 | 7/2014 | Nilsson et al. |
| 2015/0024049 A1 | 1/2015 | Nilsson et al. |
| 2015/0209318 A1 | 7/2015 | Goldman et al. |
| 2015/0272894 A1 | 10/2015 | Nilsson et al. |
| 2018/0055804 A1 | 3/2018 | Vaughn et al. |
| 2018/0055806 A1 | 3/2018 | Dyakonov et al. |
| 2018/0185319 A1 | 7/2018 | Goldman et al. |
| 2018/0263946 A1 | 9/2018 | Goldman et al. |
| 2018/0278918 A1 | 9/2018 | Peri |
| 2019/0008768 A1 | 1/2019 | Zawaneh et al. |
| 2019/0091191 A1* | 3/2019 | Nilsson ............... A61K 31/225 |
| 2019/0091192 A1* | 3/2019 | Nilsson ............... A61K 31/225 |
| 2019/0091193 A1* | 3/2019 | Nilsson ............... A61K 31/225 |
| 2019/0117613 A1 | 4/2019 | Nilsson et al. |
| 2019/0201368 A1 | 7/2019 | Nilsson et al. |
| 2019/0358190 A1 | 11/2019 | Goldman et al. |

FOREIGN PATENT DOCUMENTS

| | | |
|---|---|---|
| AU | 2013204286 B2 | 5/2017 |
| AU | 2017200394 B2 | 12/2018 |
| CN | 1433303 | 7/2003 |
| CN | 1487828 | 4/2004 |
| CN | 1600100 A | 3/2005 |
| CN | 101056624 | 10/2007 |
| CN | 101318901 A | 12/2008 |
| CN | 101475477 A | 7/2009 |
| CN | 101701943 A | 5/2010 |
| DE | 25 30 372 | 1/1977 |
| DE | 2621214 A1 | 11/1977 |
| DE | 27 03 964 | 8/1978 |
| DE | 28 40 498 | 8/1979 |
| DE | 3834794 A1 | 4/1990 |
| EP | 0 312 697 | 4/1989 |
| EP | 0 349 235 | 1/1990 |
| EP | 0 518 388 | 12/1992 |
| EP | 0354921 B1 | 10/1996 |
| EP | 0605700 B1 | 5/2000 |
| EP | 1051159 B1 | 4/2002 |
| EP | 1123092 B1 | 8/2002 |
| EP | 0699070 B1 | 9/2002 |
| EP | 2316430 A1 | 5/2011 |
| EP | 2056834 B1 | 8/2012 |
| EP | 1485078 B1 | 9/2012 |
| EP | 2379063 B1 | 3/2013 |
| EP | 2564839 B1 | 5/2016 |
| GB | 1153927 A | 6/1969 |
| WO | WO 1989001930 | 3/1989 |
| WO | WO 1995030422 A1 | 11/1995 |
| WO | WO 1996019184 | 6/1996 |
| WO | WO 1996032942 | 10/1996 |
| WO | WO 1997048371 | 12/1997 |
| WO | WO 1998004290 | 2/1998 |
| WO | WO 1998035666 | 8/1998 |
| WO | WO 1998052549 | 11/1998 |
| WO | WO 1999049858 | 10/1999 |
| WO | WO 2000012072 | 3/2000 |
| WO | WO 2000023068 A2 | 4/2000 |
| WO | WO 2000030622 A2 | 6/2000 |
| WO | WO 2001051047 | 7/2001 |
| WO | WO 2001096281 | 12/2001 |
| WO | WO 2002055063 | 7/2002 |
| WO | WO 2002055066 | 7/2002 |
| WO | WO 2002055067 | 7/2002 |
| WO | WO 2002058677 A1 | 8/2002 |
| WO | WO 2003004001 A1 | 1/2003 |
| WO | WO 2003028742 | 4/2003 |
| WO | WO 2003041705 | 5/2003 |
| WO | WO 2003080034 A2 | 10/2003 |
| WO | WO 2004018452 | 3/2004 |
| WO | WO 2004084920 | 10/2004 |
| WO | WO 2004098617 | 11/2004 |
| WO | WO 2004098618 | 11/2004 |
| WO | WO 2004098619 | 11/2004 |
| WO | WO 2004103370 | 12/2004 |
| WO | WO 2005016318 | 2/2005 |
| WO | WO 2005023241 A1 | 3/2005 |
| WO | WO 2005105099 | 11/2005 |
| WO | WO 2006037342 A2 | 4/2006 |
| WO | WO 2006050730 A1 | 5/2006 |
| WO | WO 2007005879 A2 | 1/2007 |
| WO | WO 2007006307 A2 | 1/2007 |
| WO | WO 2007006308 | 1/2007 |
| WO | WO 2007042034 | 4/2007 |
| WO | WO 2007042035 | 4/2007 |
| WO | WO 2007148744 | 12/2007 |
| WO | WO 2008096271 | 8/2008 |
| WO | WO 2008097596 A2 | 8/2008 |
| WO | WO 2009005803 A1 | 1/2009 |
| WO | WO 2010126605 A1 | 4/2010 |
| WO | WO 2010079221 A1 | 7/2010 |
| WO | WO 2010079222 | 7/2010 |
| WO | WO 2011100589 A1 | 8/2011 |
| WO | WO 2012162669 A1 | 11/2012 |
| WO | WO 2012170923 A1 | 12/2012 |
| WO | WO 2013076216 A1 | 5/2013 |
| WO | WO 2013119677 A1 | 8/2013 |
| WO | WO 2014031844 A1 | 2/2014 |
| WO | WO 2015130998 A1 | 9/2015 |
| WO | WO 2016057133 A1 | 4/2016 |
| WO | WO 2017040272 A1 | 3/2017 |
| WO | WO 2017151184 A1 | 9/2017 |

OTHER PUBLICATIONS

Litjens et al., 2004, "Pharmocokinetics of oral fumarates in healthy subjects", Br. J. Clin. Pharmacol., 58(4):429-432.
Kreuter et al., 2002, "Treatment of disseminated granuloma annulare with fumaric acid esters," BMC Dermatology, vol. 2, No. 5.
Reddingius, W. G., 1997, "Bioanalysis and Pharmacokinetics of Fumarates in Humans," Dissertation ETH Zurich No. 12199.
Olsson, 1995, "Cytokine-producing Cells in Experimental Autoimmune Encephalomyelitis and Multiple Sclerosis," Neurology, Jun. 1995.
Del Prete, "The Concept of Type-1 and Type-2 helper T cells and their Cytokines in Humans," Faculty of Medicine, Uni. of Florence, Italy; Sep. 1996.
Roll et al., 2007, "Use of Fumaric Acid Esters in Psoriasis," Department of Dermatology, Hamburg Germany 2007, vol. 73, Issue 2.
China Application No. 200680041526.8: Office Action dated Jan. 15, 2010 citing reference for ISBN 7-5025-6620-1, both documents in Chinese with English translations.
Agarwal et al., "[P07.102] Effects of BG-12 on quality of life in patients with relapsing-remitting multiple sclerosis: Findings from the DEFINE study," Neurology 78:P07.102 (2012).
Albrecht et al., "[P02.120] Dimethylfumarate protects from oxidative stress by increasing glutathione," Neurology, 78:P02.120 (2012).
Anon., "BG 12: BG 00012, BG 12/Oral Fumarate, FAG-201, second-generation fumarate derivative—Fumapharm/Biogen Idec," Drugs RD 6:229-230 (2005).

(56) References Cited

OTHER PUBLICATIONS

Anon., "Handbook of Pharmaceutical Excipients" entry for Ethylcellulose, translated into Japanese by the Pharmaceutical Society of Japan, pp. 44-47 (1989).
Anon., "Handbook of Pharmaceutical Excipients" entry for Polyethyleneglycol, translated into Japanese by the Pharmaceutical Society of Japan, pp. 334-340 (1989).
Anon., "Handbook of Pharmaceutical Excipients" entry for Hydroxypropyl cellulose, translated into Japanese by the Pharmaceutical Society of Japan, pp. 281-285 (1989).
Anon., "Handbook of Pharmaceutical Excipients" entry for Methacrylic acid copolymer, polymericmethacrylates, translated by the Pharmaceutical Society of Japan, pp. 359-361 (1989).
Arnold et al., "[IN3-2.002] Effect of BG-12 on brain atrophy and lesions volume: MRI results from the DEFINE study during first and second year of treatment," Neurology 78:IN3-2.002 (2012).
Arnold et al., "[P02.121] Neuroprotective effects of BG-12 on malonate-induced striatal lesion volume in Sprague-Dawley rat brain," Neurology 78:P02.121 (2012).
Arnold et al., "[S11.003] Effect of BG-12 on brain atrophy and lesions volume: MRI results from the DEFINE study during first and second year of treatment," Neurology 78:S11.003 (2012).
Arnold et al., "[S11.004] Effects of BG-12 on magnetization transfer ratio in whole brain and normal-appearing brain tissue: Findings from the DEFINE study," Neurology 78:S11.004 (2012).
Arnold et al., "Efficacy on MRI endpoints of BG-12, an oral therapy, in relapsing-remitting multiple sclerosis: data from the phase 3 DEFINE trial," Mult. Scler. J. 17:S369 (Abstract P831) (2011).
Asadullah et al., "Influence of monomethylfumarate on monocytic cytokine formation—explanation for adverse and therapeutic effects in psoriasis?," Arch. Dermatol. Res. 289:623-630 (1997).
Balasubramaniam et al., "Fumaric acid esters in severe psoriasis, including experience of use in combination with other systemic modalities," Br. J. Dermatol. 150:741-746 (2004).
Bar-Or et al., "[P01.130] Effect of BG-12 in subgroups of patients with relapsing-remitting multiple sclerosis: Findings from the DEFINE study," Neurology 78:P01.130 (2012).
Beebe et al., "[P05.034] The active metabolite of BG-12, monomethyl fumarate ils transported across the blood-brain barrier: single- and multiple-dose studies in mice," Annual Meeting of the American Academy of Neurology 2011 Session P05: Multiple Sclerosis: Models (Apr. 13, 2011).
Bista et al., "[P02.108] Dimethyl fumarate suppresses inflammation in vitro via both Nrf2-dependent and Nrf2-independent pathways," Neurology 78:P02.108 (2012).
Feinstein et al., "BG-12 exhibits anti-inflammatory and prometabolic effects in brain astrocytes," Mult. Scler. J. 16:S309 (Abstract P879) (2010).
Fox et al., "(S34) Phase 3 clinical program to assess efficacy and safety of BG00012 in MS," Int. J. MS Care 9:59 (Abstract S34) (2007).
Fox et al., "[S01.003] Clinical efficacy of BG-12 in relapsing-remitting multiple sclerosis (RRMS): Data from the phase 3 CONFIRM study," Neurology 78:S01.003 (2012).
Fox et al., "Placebo-controlled phase 3 study of oral BG-12 or glatiramer in multiple sclerosis," N. Engl. J. Med.367:1087-1097 (2012).
Friedrich et al., "Addition of pentoxifylline could reduce the side effects of fumaric acid esters in the treatment of psoriasis," Acta Derm. Venereol. 81:429-430 (2001).
Giovannoni et al., "[PD5.005] BG-12 increases the proportion of patients free of clinical and radiologic disease activity in relapsing-remitting multiple sclerosis: Findings from the DEFINE study," Neurology 78:PD5.005 (2012).
Gold et al., "Clinical efficacy of BG-12, an oral therapy, in relapsing-remitting multiple sclerosis: Data from the phase 3 DEFINE trial," Mult. Scler. J. 17:S34 (Abstract 95) (2011).
Gold et al., "Safety of a novel oral single-agent fumarate, BG00012, in patients with relapsing-remitting multiple sclerosis: results of a phase 2 study," J. Neurol. 253 [Suppl 2]: 11/144-145 (Abstract P573) (2006).
Gold et al., "Two phase 3 studies to determine the efficacy and safety of BG00012, a novel, oral fumaric acid derivative, in patients with relapsing multiple sclerosis," Mult. Scler. 13:S173 (Abstract P579) (2007).
Gold et al., "Placebo-controlled phase 3 study of oral BG-12 for relapsing multiple sclerosis," N. Engl. J. Med. 367:1098-1107 (2012).
Jin et al., "Novel dosage form of controlled release of drug," Chemical Industry Press, p. 109 (2005) (English Language Translation Provided) (4 pages).
Kappos et al., "BG-12 effects on patient-reported outcomes in relapsing-remitting multiple sclerosis: Results from the DEFINE study," Mult. Scler. J. 17:S488 (Abstract P1071) (2011).
Kappos et al., "Efficacy and safety of oral fumarate in patients with relapsing-remitting multiple sclerosis: a multicentre, randomised, double-blind, placebo-controlled phase IIb study," Lancet 372:1463-1472 (2008).
Kappos et al., "Efficacy of a novel oral single-agent fumarate, BG00012, in patients with relapsing-remitting multiple sclerosis: results of a phase 2 study," J. Neurol. 253 [Suppl 2]:11/27 (Abstract 0108) (2006).
Kolbach et al., "Fumaric acid therapy in psoriasis: Results and side effects of 2 years of treatment," J. Am. Acad. Dermatol. 27:769-771 (1992).
Kreuter et al., "Fumaric acid esters in necrobiosis lipoidica: Results of a prospective noncontrolled study," Br. J. Dermatol. 153:802-807 (2005).
Lee et al., "Spotlight on fumarates," Int. MS J. 15:12-18 (2008).
Lehmann et al., "Fumaric acid esters are potent immunosuppressants: Inhibition of acute and chronic rejection in rat kidney transplantation models by methyl hydrogen fumarate," Arch. Dermatol. Res. 294:399-404 (2002).
Linker et al., "[P07.196] Superior effects of combination therapy with BG-12 (dimethylfumarate) and interferon beta in experimental autoimmune encephalomyelitis," Annual Meeting of the American Academy of Neurology 2011 Session PO7: Multiple Sclerosis: Interventions IV (Apr. 14, 2011).
Litjens et al., "Monomethylfumarate affects polarization of monocyte-derived dendritic cells resulting in down-regulated Th1 lymphocyte responses," Eur. J. lmmunol. 34:565-575 (2004).
Macmanus et al., "BG-12 reduces evolution of new enhancing lesions to T1-hypointense lesions in patients with multiple sclerosis," J. Neurol. 258:449-456 (2011).
Methner et al., "[P01.200] Dimethylfumarate protects hippocampal cells from oxidative stress by increasing glutathione," Annual Meeting of the American Academy of Neurology 2011 Session P01:Multiple Sclerosis: Medication Safety: Long Term Follow-Up (Apr. 11, 2011).
Miller et al., "[S11.001] Effects of BG-12 on magnetic resonance imaging (MRI) endpoints in patients with relapsing-remitting multiple sclerosis (RRMS): Data from the phase 3 CONFIRM study," Neurology 78:S11.001 (2012).
Mrowietz et al.,"Treatment of severe psoriasis with fumaric acid esters: Scientific background and guidelines for therapeutic use. The German Fumaric Acid Ester Consensus Conference," Br. J. Dermatol. 141:424-429 (1999).
Phillips et al., "[S41.005] Safety and tolerability of BG-12 in patients with relapsing-remitting multiple sclerosis (RRMS): analyses from the CONFIRM study," Neurology 78:S41.005 (2012).
Scannevin et al., "[P05.037] Neuroprotective effects of BG-12 and other fumarates on primary cultures of neurons and astrocytes after oxidative challenge," Annual Meeting of the American Academy of Neurology 2011 Session P05: Multiple Sclerosis: Models (Apr. 13, 2011).
Scannevin et al., "Neuroprotective effects of dimethyl fumarate and monomethyl fumarate on primary cultures of human spinal cord astrocytes after oxidative challenge," Mult. Scler. J. 16:S312 (2010) (Abstract P887).

(56) References Cited

OTHER PUBLICATIONS

Schilling et al., "Fumaric acid esters are effective in chronic experimental autoimmune encephalomyelitis and suppress macrophage infiltration," Clin. Exp. lmmunol. 145:101-107 (2006).
Schimrigk et al., "Oral fumaric acid esters for the treatment of active multiple sclerosis: an open-label, baseline-controlled pilot study," Eur. J. Neurol. 13:604-610 (2006).
Sebok et al., "Effect of fumaric acid, its dimethylester, and topical antipsoriatic drugs on epidermal differentiation in the mouse tail model," Skin Pharmacol. 9:99-103 (1996).
Selmaj et al., "Safety and tolerability of BG-12 in the phase 3 DEFINE trial in patients with relapsing-remitting multiple sclerosis," Mult. Scler. J. 17:S451 (2011) (Abstract P994).
Sheikh et al., "[P04.136] Safety, tolerability, and pharmacokinetics of BG-12 administered with and without aspirin: key findings from a randomized, double-blind, placebo-controlled trial in healthy volunteers," Neurology 78:P04.136 (2012).
Van Horssen et al., "[P02.183] BG-12 (Dimethyl Fumarate): A novel therapeutic to promote oligodendrocyte survival?," Annual Meeting of the American Academy of Neurology 2011, Session P02: Multiple Sclerosis: Immunology I (Apr. 12, 2011).
Werdenberg et al., "Presystemic metabolism and intestinal absorption of antipsoriatic fumaric acid esters," Biopharm. Drug Dispos. 24:259-273 (2003).
Woodworth et al., "Oral BG-12 in combination with interferon beta-1a or glatiramer acetate: pharmacokinetics, safety and tolerability," Mult. Scler. J. 16:S160 (2010) (Abstract P478).
International Search Report for International Application No. PCT/DK2006/000402, completed Dec. 13, 2006, dated Dec. 20, 2006 (4 pages).
International Preliminary Report on Patentability for International Application No. PCT/KD2006/000402, dated Jan. 9, 2008 (7 pages).
Written Opinion of the International Searching Authority for International Application No. PCT/DK2006/000402, completed Dec. 13, 2006 (6 pages).
International Search Report for International Application No. PCT/DK2006/000403, completed Aug. 28, 2006, dated Sep. 25, 2006 (3 pages).
International Preliminary Report on Patentability for International Application No. PCT/DK2006/000403, dated Jan. 9, 2008 (8 pages).
Written Opinion of the International Searching Authority for International Application No. PCT/DK2006/000403, completed Aug. 28, 2006, (7 pages).
International Search Report for International Application No. PCT/DK2005/000648, completed May 17, 2006, dated May 23, 2006 (6 pages).
International Preliminary Report on Patentability for International Application No. PCT/DK2005/000648, dated May 4, 2007 (10 pages).
Written Opinion of the International Searching Authority for International Application No. PCT/DK2005/000648, completed May 17, 2006 (7 pages).
PCT Demand for International Application No. PCT/DK2005/000648, dated Aug. 23, 2006, receipt date of Aug. 25, 2006 (16 pages).
International Search Report for International Application No. PCT/DK2006/000561, completed Feb. 1, 2007, dated Feb. 14, 2007 (5 pages).
International Preliminary Report on Patentability for International Application No. PCT/DK2006/000561, dated Apr. 8, 2007 (10 pages).
Written Opinion for International Application No. PCT/DK2006/000561, completed Feb. 1, 2007 (9 pages).
International Search Report for International Application No. PCT/DK2006/000563, completed Mar. 23, 2007, dated Apr. 4, 2007 (10 pages).
International Preliminary Report on Patentability for International Application No. PCT/DK2006/000563, dated Apr. 8, 2008 (11 pages).
Written Opinion of the International Searching Authority for International Application No. PCT/DK2006/000563, completed Mar. 23, 2007(10 pages).
International Search Report for International Application No. PCT/EP2010/050172, completed Mar. 25, 2010, dated Apr. 13, 2010 (2 pages).
International Preliminary Report on Patentability for International Application No. PCT/EP2010/050171, dated Jul. 12, 2011 (5 pages).
International Preliminary Report on Patentability for International Application No. PCT/EP2010/050172 with annexes, dated Apr. 5, 2011 (33 pages).
Written Opinion of the International Searching Authority for International Application No. PCT/EP2010/050172, completed Mar. 25, 2010, dated Apr. 13, 2010 (6 pages).
PCT Demand for International Application No. PCT/EP2010/050172, dated Nov. 9, 2010 (35 pages).
Communication Pursuant to Article 94(3) EPC for European Patent Application No. 05789026.1, dated Sep. 11, 2008 (3 pages).
Reply to Communication Pursuant to Article 94(3) EPC for EP patent application No. 05789026.1, dated Mar. 23, 2009 (20 pages).
Reply to Communication Pursuant to Rule 112(1) EPC for EP Application No. 05789026.1, dated Mar. 5, 2010 (21 pages).
Communication Pursuant to Article 96(2) EPC for European Patent Application No. 05800741.0, dated Aug. 30, 2007 (4 pages).
Reply to Communication Pursuant to Article 96(2) EPC for European Patent Application No. 05800741.0, dated Mar. 10, 2008 (8 pages).
Communication Pursuant to Article 94(3) EPC for EP Patent Application No. 06753339.8, dated Jul. 14, 2008 (2 pages).
Reply to Communication Pursuant to Article 94(3) EPC for EP Patent Application No. 06753339.8, dated Jan. 23, 2009 (16 pages).
Communication Pursuant to Article 94(3) EPC for EP Patent Application No. 06753339.8, dated Aug. 9, 2010 (3 pages).
Communication Pursuant to Article 94(3) EPC for European Patent Application No. 06753340.6, dated Jun. 13, 2008 (4 pages).
Reply to Communication Pursuant to Article 94(3) EPC for European Patent Application No. 06753340.6 dated Dec. 15, 2008 (19 pages).
Communication Pursuant to Article 94(3) EPC for European Patent Application No. 06753340.6, dated Jan. 9, 2009 (3 pages).
Reply to Communication Pursuant to Article 94(3) EPC for European Patent Application No. 06753340.6, dated May 4, 2009 (4 pages).
Communication Pursuant to Article 94(3) EPC for European Patent Application No. 06791453.1, dated Nov. 13, 2008 (11 pages).
Reply to Communication Pursuant to Article 94(3) EPC for European Patent Application No. 06791453.1, dated Apr. 17, 2009 (18 pages).
Communication Pursuant to Rule 62 EPC for European Patent Application No. 10182198.1, dated Mar. 28, 2011 (7 pages).
Reply to Communication Pursuant to Rules 161/162 EPC for European Patent Application No. 10700730.4, dated Jan. 20, 2012 (51 pages).
Communication Pursuant to Article 94(3) EPC for European Patent Application No. 10700730.4, dated May 30, 2012 (3 pages).
First Office Action issued in Chinese Patent Application No. 200580038572.8, dated Feb. 6, 2009 (English Language Translation Provided) (12 pages).
Second Office Action issued in Chinese Patent Application No. 200580038572.8, dated Nov. 27, 2009 (English Language Translation Provided) (11 pages).
Third Office Action issued in Chinese Patent Application No. 200580038572.8, dated Aug. 25, 2010 (English Language Translation Provided) (13 pages).
Fourth Office Action issued in Chinese Patent Application No. 200580038572.8, dated Feb. 11, 2011 (English Language Translation Only) (5 pages).
First Examination Report issued in Indian Patent Application No. 1583/KOLNP/2007, dated Jan. 3, 2011 (3 pages).
First Office Action issued in Japanese Patent Application No. 2007-535023, dated Oct. 4, 2011 (English Language Translation Provided) (7 pages).

(56) References Cited

OTHER PUBLICATIONS

Final Office Action issued in Japanese Patent Application No. 2007-535023, dated Aug. 7, 2012 (English Language Translation Provided) (7 pages).
English Language Translation of the First Office Action issued in Chinese Patent Application No. 201080011787.1, dated Dec. 3, 2012 (24 pages).
Notice of Opposition to a European Patent No. 2 316 430, filed by Zentiva k.s., dated Mar. 5, 2013 (13 pages).
"Rote Liste" 2000, p. 32/315, "Fumaderm" (No English Language Translation).
Lachman et al., The Theort and Practice of Industrial Pharmact, Third Edition. Lordi, "Chapter 14: Sustained Release Dosage Forms," pp. 430-456 (30 pages).
Mrowietz et al., "Treatment of Psoriasis with Fumaric Acid Esters: Results of a Prospective Multicentre Study," Br. J. Derm. 138:456-460 (1998).
Notice of Opposition to a European Patent No. 2 316 430, filed by Dr. Christian Hollatz dated Mar. 6, 2013 (18 pages).
Kunst, "Fumaarzuurtherapie bij psoriasis," TIG pp. 243-251 (1998) (English Language Translation Provided).
English Language Information Leaflet "Psoriasis" by the Psorinovo Association (www.osoriasistheraoie.nl).
List of medicaments on offer from Mierlo Hoult Phramacy, Netherlands, including Psoinovo® 30 mg and 120 mg, dated Jan. 1, 2004.
In vitro dissolution test of Psorinovo tablet dated Mar. 6, 2013.
"Rote Liste" 1997, p. 32/330, "Fumaderm".
Excerpt from Bauer and Fremming, "Lehrbuch der pharmazeutischen Technologie,"Wissenschaftliche Verlaqsqesellschaft Stuaaart, p. 371, 2002.
Haan et al., "Oral Controlled Release Dosage Forms. A Review," Pharmaceutisch Weekblad Scientific Edition 6:57-67, 1984.
Malka et al., "Controlled Delivery of Fumaric Acid—A New Possibility in the Treatment of Psoriasis," Proceed. Intl. Symp. Control. Bioact. Mater. 25:836-837, 1998.
Notice of Opposition to a European Patent No. 2 316 430, filed by Apotheek Mierlo-Hout, dated Mar. 6, 2013 (44 pages).
Kreuter et al., "Treatment of Disseminated Granuloma Annul are with Fumaric Acid Esters," BMC Dermatology 2:5 (2002) (3 pages).
Mrowietz et al., "Treatment of Severe Psoriasis with Fumaric Acid Esters: Scientific Background and Guidelines for Therapeutic Use," Br. J. Dermatol. 141:424-429 ( 1999).
Najarian et al., "Connections between Psoriasis and Crohn's Disease," J. Am. Acad. Dermatol. 48:805-824 (2003).
Ojetti et al., "High Prevalence of Celiac Disease in Psoriasis," Am. J. Gastroenterol. 98:2574-2575 (2003).
"Aqueous EUDRAGIT" "Coatings Enable GI Targeting with Capsules," Pharma Polymers News No. 8, pp. 1-2, Oct. 2001.
"It is Not Only the Polymer that Determines the Properties of the Dosage Form," Pharma Polymers News No. 8, pp. 3-4, Oct. 2001.
"EUDRAGIT® Makes it Possible," Pharma Polymers News No. 7, p. 1, Oct. 2000.
"New Colon Delivery System Developed," Pharma Polymers News No. 7, pp. 2-3, Oct. 2000.
"New Formulation with EUDRAGIT" "FS 30 D Conveys the Active to the Colon," Pharma Polymers News No. 7, p. 4, Oct. 2000.
"Product Line Pharma Polymers Opens Technical Service Centers in Singapore, Shanghai and Mumbai," Pharma Polymers News No. 7, p. 5, Oct. 2000.
"EUDRAGIT" "RURS 30 D Provides for Osmotically Controlled Drug Release at Reduced Risk," Pharma Polymers News No. 7, p. 6, Oct. 2000.
Analyserapport, "dimethylfumaraat, tabletten," RegiLabs BV, dated Sep. 24, 2009 (No English Language Translation) (26 pages).
Notice of Opposition to a European Patent No. 2 316 430, filed by Synthon B.V., dated Mar. 6, 2013 (35 pages).
Exhibit A of Submission Applicant: Preparation of Erosion Matrix Tablets dated Mar. 5, 2010 for EP1799196 (1 page).
Declaration of Dominique van de Kamp, dated Mar. 5, 2013 (4 pages).
Lieberman et al., Pharmaceutical Dosage Forms: Tablets vol. 3, Second Edition, pp. 199,200,275,276 (1990).
Ansel, Introduction to Pharmaceutical Dosaae Forms 4th Edition, pp. 167, 170-174 (1985).
Van Loenen et al., "Fumaarzuurtherapie: van ficte tot werkelijkheid," Pharmaceutisch Weekb/ad 124:894-900 (1989) (English Language Abstract).
Nieboer et al., "Systemic Therapy with Fumaric Acid Derivates: New Possibilities in the Treatment of Psoriasis," J. Am. Acad. Dermatol. 20:601-608 (1989).
Nieboer et al., "Fumaric Acid Therapy in Psoriasis: A Double-Blind Comparison Between Fumaric Acid Compound Therapy and Monotherapy with Dimethylfumaric Acid Ester," Dermatologica 181:33-37 (1990).
Notice of Opposition to a European Patent No. 2 316 430, filed by Biogen Idec, dated Mar. 6, 2013 (44 pages).
Hagers Handbuch der pharmazeutischen Praxis. 2 Methoden. p. 955 (1991) (No English Language Translation).
SmPC of Fumaderm® initial/Fumaderm®, published Jan. 2004 (9 pages) (No English Language Translation Provided).
Bacharach-Buhles et al., "Fumaric Acid Esters (FAEs) Suppress CD 15- and ODP 4-Positive Cells in Psoriasis," Acta. Derm. Venerol. (Stockh) Suppl. 186:79-82 (1994).
Bauer et al., "5.4 Biopharmazeutische Probleme und Grenzen der Wirksamkeit von Uberzugen auf Arzineiformen," pp. 136-139 in Oberzogene Arzneiformen. (1988) (No English Language Translation Provided).
Voigt, Excerpt from "Lehrbuch der pharmazeutischen Technologie," pp. 209-212, published 1987.
Malka et al., "Controlled Delivery of Fumaric Acid—A New Possibility in the Treatment of Psoriasis," Proceed. Intl. Svmo. Control. Rel. Bioact. Mater. 25:836-837, 1998.
Durlinger (editor) et al., "Fumaarzuur" Psoriant, Jan. 2004, vol. 22, pp. 1-36 (2004) (English Language Translation Provided).
De Apotheek, Website excerpt from http://mierlohout.nl, 2003 (6 pages).
Declaration of Jacobus C. Rasser, Ph.D. and Annexes 1-7, dated Mar. 4, 2013 (14 pages).
Declaration of Constance Yeung, Ph.D. and Annexes 1-6, dated Mar. 4, 2013 (13 pages).
Declaration of David Goldman, Ph.D., dated Feb. 27, 2013 (2 pages).
Declaration of Oliver Schinzinger, Ph.D., dated Mar. 4, 2013 (2 pages).
Declaration of Pierre Boulas, Ph.D., Michael Szulc, Ph.D., and Yiging Lin, Ph.D., and Annexes 1-4 dated Mar. 6, 2013 (43 pages).
Notice of Opposition to a European Patent No. 2 316 430, filed by Acino Pharma AG dated Mar. 5, 2013 (21 pages).
Notice of Opposition to a European Patent No. 2 316 430, filed by Medac Gesellschaft fur klinische Spezialpraparate mBh, dated Mar. 6, 2013 (30 pages).
Langguth et al., "Biopharmazie," Weinheim, pp. 271-272, 2004 (No English Language Translation Provided).
Communication pursuant to rule 114(2) EPC enclosing third party observations filed in EP1799196, dated Apr. 16, 2013 (418 pages).
Breuer et al., "Therapy of noninfectious granulomatous skin diseases with fumaric acid esters," Br J Dermatol. 152:1290-1295 (2005).
Brune et al., "Oral fumaric acid ester therapy (FAE) influence T-helper cells apoptosis in peripheral blood lymphocytes (PBLS) and soluble intercellular adhesion molecule-I (SICAM-1) in serum of patients with relapsing-remitting multiple sclerosis (RRMS)," J. Neurol. 246(Suppl. I): 1/61. P272. (Ninth Meeting of the European Neurological Society Jun. 5-9, 1999, Milan, Italy).
Brune et al., "Oral fumarate therapy alters cytokine production in patients with relapsing-remitting multiple sclerosis," vol. 10, Supplement 2, Poster P643, Sep. 2004. (ECTRIMS 04: 20th Congress of the European Committee for Treatment and Research in Multiple Sclerosis Oct. 6-9, 2004, Austria Center, Vienna, Austria).
Brune et al., "Oral fumarate therapy alters cytokine production in patients with relapsing-remitting multiple sclerosis," Multiple Scle-

(56) References Cited

OTHER PUBLICATIONS rosis, vol. 10, Supplement 2, Sep. 2004. Abstract P643, (ECTRIMS 04: 20th Congress of the European Committee for Treatment and Research in Multiple Sclerosis Oct. 6-9, 2004, Austria Center, Vienna, Austria).

Christophers, Berlin, lmmunomodulation durch Fumaderm, Chante-Berlin, Symposium (Nov. 1-3, 1996).

Coras et al., "Fumaric acid esters therapy: a new treatment modality in pityriasis rubra pilaris?," Br J Dermatol. 152:388-389 (2005).

De Jong et al., "Selective stimulation of T helper 2 cytokine responses by the anti-psoriasis agent monomethylfumarate," Eur. J. lmmunol. 26:2067-2074 (1996).

Eberlein-Konig et al., "Disseminated granuloma annulare—treatment with fumaric acid esters," Dermatology 210:223-226 (2005).

Fox et al., "CONFIRM Study Investigators. Placebo-controlled phase 3 study of oral BG-12 or glatiramer in multiple sclerosis," N. Engl J Med. 367:1087-97 (2012) (Supplementary Appendix and Protocol included).

Gambichler et al., "Clearance of necrobiosis lipoidica with fumaric acid esters," Dermatology 207:422-424 (2003).

Gold et al., "Safety of a novel oral single-age fumarate, BG00012, in patients with relapsing-remitting multiple sclerosis: results of a phase 2 study," J Neurol. 253:144-145 (2006) (Abstract P573).

Gold et al., "DEFINE Study Investigators. Placebo-controlled phase 3 study of oral BG-12 for relapsing multiple sclerosis," N Engl J Med. 367:1098-107 (2012) (Supplementary Appendix and Protocol included).

Gutzmer et al., "Successful therapy of annular elastolytic giant cell granuloma with fumaric acid esters," Dermatology 205:421-424 (2002).

Heinz et al., "Improvement of noninfectious uveitis with fumaric acid esters: results of a pilot study," Arch Ophthalmol. 125:569-571 (2007).

Kappos et al., "Efficacy of a novel oral single-agent Fumarate, BG00012, in patients with relapsing-remitting multiple sclerosis: results of a phase II study," oral presentation on May 30, 2006, at the 16th Meeting of the European Neurological Society, May 27-31, 2006, Lausanne, Switzerland.

Kappos et. al., "Efficacy of a novel oral single-agent fumarate, BG00012, in patients with relapsing-remitting multiple sclerosis: results of a phase 2 study," Abstract 0108, Proceedings of the 16th Meeting of the European Neurological Society, May 27-31, 2006, Lausanne, Switzerland (Abstract Only).

Kappos et al., "The Efficacy of BG00012 in Patients With Relapsing-Remitting Multiple Sclerosis: Subgroup Analyses From the Phase 2b Study," poster from the 60th Annual Meeting of the American Academy of Neurology, Apr. 12-19, 2008, Chicago, IL, United States.

Kappos et al., "Efficacy and safety of oral fumarate in patients with relapsing-remitting multiple sclerosis: a multicentre, randomised, double-blind, placebo-controlled phase llb study," Lancet 372:1463-1472 (2008).

Kolbach et al., "Fumaric acid therapy in psoriasis: Results and side effects of 2 years of treatment," Brief Communications 27:769-771 (1992).

Kreuter et al., "Treatment of disseminated granuloma annulare with fumaric acid esters," BMC Dermatol. 2:1-4 (2002).

Kreuter et al., "Fumaric acid esters in necrobiosis lipodica: results of a prospective noncontrolled study," Br J Dermatol. 153:802-807 (2005).

Langner et al., "Fumaric acid ester for the treatment of severe forms of psoriasis: results of a phase II clinical study," Abstract PS296, Spring Symposium of the European Academy of Dermatology and Venerology (EADV) Apr. 29-May 1, 2004, Budapest, Hungary.

Langner et al., "Efficacy and safety of a new oral formulation of fumaric acid ester for the treatment of moderate to severe psoriasis," 10th International Psoriasis Symposium, Jun. 10-13, 2004, Toronto, Canada.

Langner et al., "Results of a phase II study of a novel oral fumarate, BG-12, in the treatment of severe psoriasis," Poster P075, European Congress on Psoriasis, Oct. 21-24, 2004, Paris, France.

Langner et al., "Effects of a novel oral fumarate, BG-12, in patients with severe psoriasis: results of a phase 2 extension study," Poter P06.111, Congress of the European Academy of Dermatology and Venerology (EADV), Nov. 17-21, 2004, Florence, Italy.

Langner et al., "The efficacy and safety of a novel oral formulation of dimethylfumarate, BG00012, in patients with severe psoriasis: results of a phase 2 dose-finding and safety extension study," 3rd Spring Symposium of the European Academy of Dermatology and Venerology (EADV), 2005, Sofia, Bulgaria.

Langner et al., "Results of a phase 2 dose-ranging and safety extension study of a novel oral fumarate, BG-12, in patients with severe psoriasis," Abstract P2787, J. Am. Acad. Dermatol. p. P193, 2005.

Loewe et al., "Dimethyfumarate impairs melanoma growth and metastasis," Cancer Res. 66:11888-11896 (2006).

Memorandum of Meeting Minutes for the meeting held on Aug. 30, 2006, between attendees from the FDA and Biogen Idec regarding the End of Phase 2 for application PINO 73,061, BG00012.

Mrowietz et al., "Efficacy, safety, and quality of life effects of a novel oral formulation of dimethyl fumarate in patients with moderate to severe plaque psoriasis: results of a phase 3 study," 64th Annual Meeting of the American Academy of Dermatology, Mar. 3-7, 2006, San Francisco, California.

Nibbering et al., "Effects of monomethylfumarate on human granulocytes," J Invest Dermatol. 101:37-42(1993).

Nowack et al., "Successful treatment of recalcitrant cutaneous sarcoidosis with fumaric acid esters," BMC Dermatol. 2:1-5 (2002).

Ockenfels et al., "The antipsoriatic agent dimethylfumarate immunomodulates T-cell cytokine secretion and inhibits cytokines of the psoriatic cytokine network," Br J Dermatol. 139:390-395 (1998).

Reddingius, "Bioanalysis and pharmacokinetics of fumarates in humans," Dissertation ETH Zurich No. 12199 (1997) (149 pages).

Schimrigk et al., "Oral fumaric acid ester FAE in relapsing-remitting multiple sclerosis (RRMS). A short term, open, clinical, immunological and magnetic resonance imaging (MRI) controlled phase II trial," J. Neurol. 246(Suppl. I): 1/36 Abstract 144. (Ninth Meeting of the European Neurological Society Jun. 5-9, 1999, Milan, Italy).

Schimrigk et al., "A prospective, open-label, phase II study of oral fumarate therapy for the treatment of relapsing-remitting multiple sclerosis," Multiple Sclerosis, vol. 10, Supplement 2, Abstract P642, Sep. 2004. (ECTRIMS 04: 20th Congress of the European Committee for Treatment and Research in Multiple Sclerosis Oct. 6-9, 2004, Austria Center, Vienna, Austria).

Schimrigk et al., "A prospective, open-label, phase II study of oral fumarate therapy for the treatment of relapsing-remitting multiple sclerosis," vol. 10, Supplement 2, Poster P642, Sep. 2004. (ECTRIMS 04: 20th Congress of the European Committee for Treatment and Research in Multiple Sclerosis Oct. 6-9, 2004, Austria Center, Vienna, Austria).

Schimrigk et al., "Oral fumaric acid esters for the treatment of active multiple sclerosis: an open-label, baseline-controlled pilot study," European Journal of Neurology 13:604-610 (2006).

Schulze-Dirks et al., "Granuloma anulare disseminatum—erfolgreiche thempie mit fumarsauresster," Der Hautarzt 52:228-230 (2001) (No English language translation provided).

Sebok et al., "Antiproliferative and cytotoxic profiles of antipsoriatic fumaric acid derivatives in keratinocyte cultures," Eur J Pharmacol. 270:79-87 (1994) (Abstract Only).

Sebok et al., "The antipsoriatic dimethyl-fumarate suppresses interferon—induced ICAM-1 and HLA-DR expression on hyperproliferative keratinocytes. Quantification by a culture plate-directed APAAP-ELISA technique," Eur J Dermatol. 8:29-32 (1998).

Thio et al., "Fumaric acid derivatives evoke a transient increase in intracellular free calcium concentration and inhibit the proliferation of human keratinocytes," Br J Dermatol. 131:856-861 (1994).

(56) References Cited

OTHER PUBLICATIONS

Vandermeeren et al., "Dimethylfumarate is an inhibitor of cytokine-induced E-selectin, VCAM-1, and ICAM-1 expression in human endothelial cells," Biochem Biophys Res Commun. 234:19-23 (1997).
Official Title: "Double-blind, placebo-controlled, dose-ranging study to determine the efficacy and safety of BG00012 in subjects with relapsing-remitting multiple sclerosis," View of NCT00168701 on Sep. 14, 2005: ClinicalTrials.gov Archive.
"Oral compound BG-12 achieves primary endpoint in phase 11 study of relapsing-remitting MS with BG-12 led to statistically significant reduction in MRI measures," Biogen Idec News Release, May 30, 2006.
Kooijman et al., "Dimethyl fumarate," Acta Crystallographica E60:o917-o918 (2004).
Notice of Opposition to a European Patent filed by Mylan in European Patent No. EP2137537 (dated Feb. 28, 2014).
D3—Wierinckx et al., "Detoxication enzyme inducers modify cytokine production on rat mixed glial cells," Journal of Neuroimmunology, vol. 166, No. 1-2, Sep. 1, 2005, pp. 132-143.
D4—Gold et al., "Safety of a novel oral single-agent fumarate, BG00012, in patients with relapsing-remitting multiple sclerosis: result of a phase 2 study," Journal of Neurology, (Suppl. 2), May 2006, pp. ii144-ii144; P573.
D6—Declaration and CV of Katherine T. Dawson, MD.
D7—Biogen Idec Press Release, "Biogen Idec announces positive top-line results from second phase 3 trial investigating oral BG-12 (Dimethyl Fumarate) in Multiple Sclerosis—CONFIRM Study validates strong results from BG-12's first pivotal trial," Oct. 26, 2011.
D8—Trial Watch, "Phase III success for Biogen's oral multiple sclerosis therapy," Bio Business Briefs Nat Rev Drug Disco, vol. 10, Jun. 2011, p. 404.
D9—Kappos et al., "Efficacy and safety of oral fumarate in patients with relapsing-remitting multiple sclerosis: a multicentre, randomized, double-blind, placebo-controlled phase IIb study," The Lancet, vol. 372, Oct. 25, 2008. pp. 1463-1472.
D10—Fumaderm Label.
D11—Declaration of Professor Dr. Ralf Gold and Annexes 1-11.
D11—Annex 1—CV of Prof. Dr. Ralf Gold.
D11—Annex 2—Kappos et al., "Efficacy of a novel oral single-agent fumarate, BG00012, in patients with relapsing-remitting multiple sclerosis: results of a phase 2 study," 16th Meeting of the European Neurological Society (May 30, 2006) (Abstract).
DII—Annex 3—Efficacy of a novel oral single-agent Fumarate, BG00012, in patients with relapsing-remitting multiple sclerosis: results of a phase II study, 16th Meeting of the European Neurological Society (May 30, 2006) (Slide Presentation).
D11—Annex 4—Biogen Idec Press Release: "Oral Compound BG-12 achieves primaryendpoint in phase 11 study of relapsing-remitting MS treatment; with BG-12 led to statistically significant reductions in MRI measures," May 30, 2006.
D11—Annex 5—Sheridan, "Safety profiles come to fore as more drugs approach MS market," Nature Biotechnology, vol. 30 No. 1, Jan. 2012, pp. 6-8.
D11—Annex 6—Biogen Idec Press Release, "US and EU Regulatory authorities accept oral BG-12 marketing applications for review," May 9, 2012.
D11—Annex 7—Gold, "Oral Therapies for Multiple Sclerosis: A Review of Agents in Phase III Developments for Recently Approved," CNS Drugs 2011, vol. 25, No. 1. pp. 37-52.
D11—Annex 8—Killestein, "Oral Treatment for multiple sclerosis," Lancet Neurology vol. 10, Nov. 2011, pp. 1026-1034.
D11—Annex 9—Food and Drug Administration Press Release: "FDA approves first oral drug to reduce MS relapses,".
D11—Annex 10—Decision Resources Article, "For the treatment of Multiple sclerosis, more than 85 percent of surveyed neurologists in the EU5 expect to prescribe Biogen ldec's BG-12, Sanofi/Genzyme's Aubagio and Sanofi/Genzyme/Bayer HealthCare's Lemtrada," Jun. 25, 2012.

D11—Annex 11—EMA, "Questions and answers on the ongoing review of Gilenya(fingloimod)," European Medicines Agency, EMA/43541/2012, EMEA/H/C/000539, Jan. 19, 2012, pp. 1-2.
D12—Kappos et al., "BG00012, a novel oral fumarate, is effective in patients with relapsing-remitting multiple sclerosis," Sage Journals; Multiple Sclerosis, Sep. 2006, vol. 12. p. S85, P325.
D13—Tyrell, "Biogen MS Pill with $3 Billion Potential Hits Study Goals," Bloomberg Oct. 26, 2011.
D14—Draft Summary of Product Characteristics submitted to EMA for BG-12 (redacted version).
D15—Notice of Allowance USPTO for U.S. Appl. No. 13/372,426 dated Dec. 26, 2012.
D16—Allowed Claims USPTO of U.S. Appl. No. 13/372,426.
D17—U.S. Examiner Search Comment regarding WO 2006/037342 (D5).
D19—Cover Page and English claims of EP0354921, EP0605700, EP0699070, EP1051159, EP1485078, EP2056834.
D20—Livingstone, Churchill, The Science of Dosage Form Design 2002.
D21—EMEA, "Dose Response Information to Support Drug Registration," Office of the Federal Register, 1994.
Notice of Opposition to a European Patent filed by GL Pharma GMBH in European Patent No. EP2137537 (dated Feb. 28, 2014).
Notice of Opposition to a European Patent filed by Forward Pharma A/S in European Patent No. EP2137537 (dated Feb. 28, 2014).
D4—Declaration of Prof. Dr. Ralf Gold (dated Jan. 25, 2012 as D11).
Response to Communication dated Oct. 30, 2012 pursuant to Rule 114(2) EPC filed Dec. 6, 2012 in European Patent EP2137537.
Notice of Opposition to a European Patent filed by European Oppositions Limited in European Patent No. EP2137537 (dated Feb. 28, 2014).
D2—Biogen Idec Press Release, May 30, 2006,entitled "Oral compound BG-12 achieves primary endpoint in phase II study of relapsing-remitting multiple sclerosis; treatment with BG-12 led to statistically significant reductions in MRI measures".
D3—Presentation by L. Kappos, May 30, 2006 entitled Efficacy of a novel oral single-agent Fumarate, BG00012, in patients with relapsing-remitting multiple sclerosis: results of a phase II study.
D4—Letter from the applicant's representative dated Jan. 25, 2013 filed in response to the summons to oral proceedings dated Jan. 23, 2013.
D5—Schimrigk et al., "Oral fumaric acid esters for the treatment of active multiple sclerosis: an open-label, baseline-controlled pilot study," European Journal of Neurology, Jun. 6, 2006, 13:604-610.
Notice of Opposition to a European Patent filed by Mr. Antony Gallafent in European Patent No. EP2137537 (dated Feb. 28, 2014).
Notice of Opposition to a European Patent filed by Zaklady Farmaceutyczne Polpharma SA in European Patent No. EP2137537 (dated Feb. 28, 2014).
D1—Request form filed to initiate the International patent application which matured into the Patent.
D1b—Assignment document transferring inventor Lukashev's rights to the invention to Biogen Idec MA Inc. (Dec. 6, 2010).
D1c—Assignment document transferring inventor O'Neill's rights to the invention to Biogen Idec MA Inc. (Oct. 27, 2011).
D2a—Fox, "BG00012—A novel oral therapy in development for the treatment of multiple scleroris," US Neurological Disease 2007, issue 2, pp. 32-36. Published Nov. 2007.
D2b—Arastoo et al., "The comparison of effect of 8 weeks aerobic and yoga training on physiological cost index in multiple sclerosis patients," Sci Med J 2011; 153-162 10(2) Published 2011.
D3—List of Clinical Trials in Multiple Sclerosis 2007, published by the National MS Society. Published 2007.
D4a—Extract from the Register of Clinical Trials in Australia and New Zealand. Published Feb. 12, 2007.
D4b—Email from Administrator of the Register of Clinical Trials in Australia and New Zealand confirming publication date of D4a (Feb. 13, 2013).
D5a—Presentation entitled "2007 Research and Development Day". Published on May 17, 2007.
D5b—Press release publicly promoting the presentation of D5a. Published May 11, 2007.

(56) References Cited

OTHER PUBLICATIONS

D6—Gold et al., "Two Phase 3 studies to determine the efficacy and safety of BG00012, a novel, oral fumaric acid derivative, in patients with relapsing multiple sclerosis," Abstract of presentation given at the 23rd ECTRIMS conference and 12th RIMS conference on Oct. 13, 2007.
D11—Kappos et al., Oral Presentations, Multiple Sclerosis, 2006, 12, S1. Published on Sep. 1, 2006.
D12—ICH Topic E4, Dose Response Information to Support Drug Registration, European Medicines Agency. Published in Nov. 1994.
D13—Guidance for Industry, Exposure-Response Relationships—Study Design, Data Analysis, and Regulatory Applications, U.S. Department of Health and Human Services et al. Published in Apr. 2003.
D14a—Summary of Product Characteristics for Tecfidera 120mg gastro resistant hard capsules. Published Feb. 13, 2014.
D14b—Summary of Product Characteristics for Tecfidera 240mg gastro resistant hard capsules. Published Feb. 13, 2014.
Notice of Opposition to a European Patent filed by Actavis Group PTC ehf in European Patent No. EP2137537 (dated Feb. 28, 2014).
MAI 1—Kappos et al., "BG 00012, a novel oral fumarate, is effective in patients with relapsing-remitting multiple sclerosis," Multiple Sclerosis Journal, Sep. 2006.
MAI 2—Declaration by Katherine T. Dawson, including exhibits A-E (submitted in U.S. Appl. No. 12/526,296).
MAI 3—U.S. National Institutes of Health, "Efficacy and safety of BG00012 in relapsing-remitting multiple sclerosis," Dec. 28, 2007, [cited Feb. 25, 2014] Available from [http://clinicaltrials.gov/archive/NCT00420212/2007 12 28].
MAI 4—U.S. National Institutes of Health, "Efficacy and safety study of BG00012 with active reference in relapsing-remitting multiply sclerosis," Jan. 2, 2008, [cited Feb. 25, 2014] Available from [http://clinicaltrials.gov/archive/NCT00451451/2008 01-02].
Notice of Opposition to a European Patent filed by Zentiva k.s. In European Patent No. EP2137537.
D6—Schimrigk et al., "Oral fumaric acid esters for the treatment of active multiple sclerosis: an open-label, baseline-controlled pilot study," European Journal of Neurology 2006; 13:604-610.
D7—Gold et al., "Safety of a novel oral single-agent fumarate, BG00012, in patients with relapsing-remitting multiple sclerosis: results of a phase 2 study," Journal of Neurology, vol. 253, No. Suppl. 2, May 1, 2006, pp. 11144-11145.
D9—Wierinckx et al., "Detoxication enzyme inducers modify cytokine production in rat mixed glial cells," Journal of Neuroimmunology 166 (2005) 132-143.
D10—ICH Topic E 4, Dose Response Information to Support Drug Registration, European Medicines Agency, Nov. 1994.
D11—Guidance for Industry, Exposure-Response Relationships—Study Design, Data Analysis, and Regulatory Applications, U.S. Department of Health and Human Services et al., Apr. 2003.
D12—Lee et al., "Spotlight on Fumarates," The International MS Journal 2008; 15: 12-18.
D13—Schilling et al., "Fumaric acid esters are effective in chronic experimental autoimmune encephalomyelitis and suppress macrophage infiltration," Clinical and Experimental Immunology (2006), 145(1), 101-107.
D14—Kappos et al., "Efficacy and safety of oral fumarate in patients with relapsing-remitting multiple sclerosis: a multicentre, randomized, double-blind, placebo-controlled phaseIIb study," Lancet 2008; 372: 1463-72.
D15—Killestein, "Oral treatment for multiple sclerosis," Lancet Neurol 2011; 10: 1026-34.
D16—Summary of Product Characteristics.
D17—Declaration of Prof. Ralf Gold (Jan. 25, 2013).
D18—Biogen Idec, Press Release of Oct. 26, 2011.
English language translation of an Official Action for Japanese Patent Application No. 2012-267572, dated Feb. 12, 2014.
Nakano M., JJSHP, 31:13-16 (1995).
Pharmaceutical Excipients Dictionary (Yakuji Nippo, Ltd.) pp. 106-107, 1994.
Sogo Seizaiqaku (General Galencial Pharmacy) (Nanzando Co., Ltd), pp. 458-459, 2000.
Pharmaceutical Excipients Reference, (Yakuii Nippo, Ltd.), pp. 11-21, 1999.
Communication pursuant to Article 94(3) EPC for European Patent Application No. 05789026.1, dated Nov. 11, 2014 (3 pages).
Extended European Search Report for European Patent Application No. 14172396.5, dated Nov. 19, 2014 (7 pages).
Communication of Third Party Observations pursuant to Article 115 EP against EP 2 801 354, dated Nov. 27, 2014 (9 pages).
Communication of Third Party Observations pursuant to Article 115 EP against EP 2 801 355, dated Nov. 26, 2014 (9 pages).
Proprietor's Observations on the Notices of Opposition of European Patent No. EP 2 137 537 filed on behalf of Biogen Idec MA Inc. dated Oct. 17, 2014 including Exhibits A through I and Documents D48 through D56 (191 pages}.
Tabandeh et al., 2003, "Preparation of Sustained-Release Matrix Tablets of Aspirin with Ethylcellulose, Eudragit RS100 and Eudragit S100 and Studying the Release Profiles and their Sensitivity to Tablet Hardness," Iranian Journal of Pharma Research, 2(4):201-206.
Thio et al., 1995, "Long-term systemic therapy with dimethylfumarate and monoethylfumarate (Fumaderm®) in psoriasis," J Eur Acad Dermatol Venereol., 4:35-40.
Mease, 2002, "Tumour necrosis factor (TNF) in psoriatic arthritis: pathophysiology and treatment with TNF inhibitors," Ann Rheum Dis., 61(4):298-304.
Mrowietz et al., 2005, "Dimethylfumarate for psoriasis: more than a dietary curiosity," Trends Mol Med., 11(1):43-48.
Treumer et al., 2003, "Dimethylfumarate is a potent inducer of apoptosis in human T cells," J Invest Dermatol., 121(6):1383-1388.
Schilling et al., 2005, "Fumarate therapy ameloriates chronic experimental autoimmune encephalomyelitis (EAE)," Clin Immunol, 115(1,Suppl. 1), Abst Sa1.04.
Kappos et al., 2005, "A randomised, placeno-controlled phase II trial of a novel oral single-agent fumarate therapy, BG00012, in patients with relapsing-remitting multiple scierosis," J Neural, 252(Suppl. 2), Abst P574.
Mrowietz et al., 2005, Spellman, M. Dimethyl fumarate (BG00012) as an oral therapy for moderate to severe psoriasis; Results of a multicenter, randomized, double-blind, placebo-controlled trial, J Invest Dermatol, 125(Suppl. 1):Abst 406.
Schimrigk et al., 2005, "An open-label prospective study of oral fumaric acid therapy for the treatment of relapsing remitting multiple sclerosis (RRMS)," Neurology, 64(6, Suppl. 1) Abst S64.003.
Schimrigk et al., 2004, "A prospective, open-label, phase II study of oral fumarate therapy for the treatment of relapsing-remitting multiple sclerosis," Multiple Scler, 10(Suppl. 2): Abst P462.
Brune et al., 2004, "Oral fumarate therapy alters cytokine production in patients with relapsing-remitting multiple sclerosis," Multiple Scler, 10(Suppl. 2): Abst P643.
Sheikh et al., 2013, "Tolerability and pharmacokinetics of delayed-release dimethyl fumarate administered with and without aspirin in healthy volunteers," Clin Ther., 35(10):1582-1594.
European Medicines Agency (EMA), Assessment Report: TECFIDERA, dated Nov. 26, 2013, pp. 1-136.
Whelan et al., 1992, "The effect of aspirin on niacin-induced cutaneous reactions," J Fam Pract., 34(2): 165-168.
Prescribing Information for TECFIDERA® (dimethyl fumarate) delayed-release capsules, revised Dec. 2017 (19 pages).
Declaration of Dr. Kevin Shakesheff filed in U.S. Appl. No. 14/209,480, dated Oct. 5, 2015.
Response to Non-Final Office Action filed on May 30, 2014 for U.S. Appl. No. 13/760,916 (17 pages).
Response to Final Office Action filed on Nov. 5, 2015 for U.S. Appl. No. 13/827,228 (13 pages).
Response to Non-Final Office Action filed on Jul. 26, 2016 for U.S. Appl. No. 13/827,228 (23 pages).
Response to Non-Final Office Action filed on Sep. 28, 2017 for U.S. Appl. No. 14/679,716 (17 pages).
Response to Final Office Action filed on Jun. 15, 2018 for U.S. Appl. No. 14/679,716 (14 pages).

(56) References Cited

OTHER PUBLICATIONS

Response to Non-Final Office Action filed on Feb. 5, 2019 for U.S. Appl. No. 15/988,568 (9 pages).
Patent Examination Report No. 1 dated Apr. 7, 2015 for Australian Application No. 2013203445 (4 pages).
Response to Patent Examination Report No. 1 filed on Sep. 2, 2016 in Australian Application No. 2013203445 (18 pages).
Response to Patent Examination Report No. 1 filed on Apr. 18, 2017 in Australian Application No. 2013204286 (7 pages).
Response to Non-Final Office Action filed on Dec. 23, 2014 for U.S. Appl. No. 13/827,228 (9 pages).
Response to Final Office Action filed on May 11, 2017 for U.S. Appl. No. 13/827,228 (22 pages).
Response to Non-Final Office Action filed on Nov. 26, 2018 for U.S. Appl. No. 14/679,716 (13 pages).
Response to Final Office Action filed on Jul. 3, 2019 for U.S. Appl. No. 14/679,716 (14 pages).
Response to Non-Final Office Action filed on Oct. 23, 2018 for U.S. Appl. No. 15/988,568 (10 pages).
European Patent Office, Decision Revoking the European Patent (Art. 101(2) and 101(3)(b) EPC) in opposition to European Patent No. 1799196 dated Feb. 15, 2019 (36 pages).
European Patent Office, Decision Revoking the European Patent (Art. 101(2) and 101(3)(b) EPC) and Annex I in opposition to European Patent No. 2316430 dated Jul. 10, 2015 (26 pages).
European Patent Office, Decision Revoking the European Patent (Art. 101(3)(b) EPC) in opposition to European Patent No. 2801354 dated Sep. 9, 2019 (39 pages).
European Patent Office, Decision Revoking the European Patent (Art. 101(3)(b) EPC) in opposition to European Patent No. 2801355 dated Mar. 22, 2018 (35 pages).
Robinson et al., 1987, "Controlled Drug Delivery—Fundamentals and Applications," Marcel Dekker, Inc., pp. 296-297 and 323-325 (submitted by Keltie LLP on Mar. 21, 2017 as D14 in opposition to European Patent No. 1799196).
Skelly et al., 1990, "In Vitro and in Vivo Testing and Correlation for Oral Controlled/Modified Release Dosage Forms. Report of the 2nd Workshop Held Dec. 1988, Washington, DC, U.S.A." Journal of Controlled Release, 14:95-106 (submitted by Keltie LLP on Mar. 21, 2017 as D15 in opposition to European Patent No. 1799196).
Bozdag et al., 1999, "Formulation and stability evaluation of enteric-coated omeprazole formulations," S.T.P. Pharma Sciences, 9(4):321-327 (submitted by Pentafarma, Sociedade Técnico-Medicinal, SA on Mar. 22, 2017 as D6 in opposition to European Patent No. 1799196).
The United States Pharmacopeia—The National Formulary, USP24, NF19, official from Jan. 1, 2000, Physical Tests / <724> Drug Release, pp. 1944-1947 (submitted by Pentafarma, Sociedade Técnico-Medicinal, SA on Mar. 22, 2017 as D7 in opposition to European Patent No. 1799196).
The United States Pharmacopeia—The National Formulary, USP24, NF19, official from Jan. 1, 2000, Physical Tests / <711> Dissolution, pp. 1941-1943 (submitted by Pentafarma, Sociedade Técnico-Medicinal, SA on Mar. 22, 2017 as D11 in opposition to European Patent No. 1799196).
Sweetser et al., 2013, "Manufacturer's Response to Case Reports of PML," N Engl J Med., 368(17):1659-1661 (submitted by HGF Limited on Sep. 12, 2017 as D35 in opposition to European Patent No. 1799196).
Forward Pharma, Results of Dissolution Test of Psorinovo tablets 30 mg dated Apr. 23, 2015, 3 pages (submitted by HGF Limited on Sep. 12, 2017 as D36 in opposition to European Patent No. 1799196).
Forward Pharma, Report on Clinical Study 102 dated May 25, 2014, 4 pages (submitted by HGF Limited on Sep. 12, 2017 as D37 in opposition to European Patent No. 1799196).
Wade et al., 1994, "Handbook of Pharmaceutical Excipients (2nd Edition) on Polymethacrylates," The Pharmaceutical Press London, pp. 362-366 (submitted by HGF Limited on Jul. 18, 2018 as D45 in opposition to European Patent No. 1799196; also submitted by HGF Limited on Mar. 7, 2019 as D46 in opposition to European Patent No. 2801354).
Gennaro, 1995, "Remington: The Science and Practice of Pharmacy—vol. II (19th Edition)" Mack Publishing Company, Easton, Pennsylvania, pp. 1653-1654 and 1660-1669 (submitted by Strawman Limited on Jul. 13, 2018 as D45 in opposition to European Patent No. 1799196; also submitted by Strawman Limited on Oct. 11, 2018 as D40 in opposition to European Patent No. 2801354).
Declaration of Christin Galetzka including Annex 1 dated Jun. 18, 2015, 4 pages (submitted by Forward Pharma A/S on Jun. 19, 2015 as D76 in opposition to European Patent No. 2316430).
Declaration of Professor Roger Verbeeck including Annexes 1-3 dated Jun. 19, 2015, 39 pages (submitted by Forward Pharma A/S on Jun. 19, 2015 as D77 in opposition to European Patent No. 2316430).
Biogen Idec Clinical Study Results relating to BG-12 for treatment of rheumatoid arthritis (unpublished results) dated Mar. 10, 2011, 9 pages (submitted by Biogen MA Inc. on Apr. 24, 2015 as D73 in opposition to European Patent No. 2316430).
Declaration of Professor John Caldwell including Annex 1 dated Apr. 23, 2015, 35 pages (submitted by Biogen MA Inc. on Apr. 24, 2015 as D74 in opposition to European Patent No. 2316430).
Declaration of Frans Durlinger dated Apr. 14, 2015, 3 pages (submitted by Mierlo-Hout Pharmacy on Apr. 14, 2015 in opposition to European Patent No. 2316430; submitted by HGF Limited on Sep. 12, 2017 as D34 in opposition to European Patent No. 1799196).
Declaration of Christin Galetzka including Annexes 1-4 dated Nov. 27, 2017, 13 pages submitted by HGF Limited on Mar. 7, 2019 as D45 in opposition to European Patent No. 2801354).
Gordon et al., 1990, "Effect of the mode of croscarmellose sodium incorporation on tablet dissolution and friability," J Pharm Sci., 79(1):43-47.
Haaf et al., 1985, "Polymers of N-Vinylpyrrolidone: Synthesis, Characterization and Uses," Polymer Jouranl, 17(1):143-152.
United States Patent Trial and Appeal Board, *Biogen MA, Inc.* (U.S. Pat. No. 8,399,514 B2) v. *Forward Pharma A/S* (U.S. Appl. No. 11/576,871), Decision on Motions, Patent Interference No. 106,023 (Mar. 31, 2017) (33 pages).
United Stapes Court of Appeals for the Federal Circuit, *FWP IP APS* v. *Biogen MA, Inc.*, Case No. 2017-2109, Decision dated Oct. 24, 2018 (Appeal from Interference No. 106,023) (20 pages).
United States Patent and Trademark Office, Non-Final Office Action with List of References dated Jun. 1, 2020 for U.S. Appl. No. 16/227,287 (17 pages).
United States Patent and Trademark Office, Non-Final Office Action with List of References dated Jun. 5, 2020 for U.S. Appl. No. 16/294,038 (14 pages).
United States Patent and Trademark Office, Final Office Action dated Jan. 12, 2021 for U.S. Appl. No. 16/294,038 (20 pages).

\* cited by examiner

CONTROLLED RELEASE PHARMACEUTICAL COMPOSITIONS COMPRISING A FUMARIC ACID ESTER

CROSS REFERENCE TO RELATED APPLICATIONS

This application is a continuation of U.S. patent application Ser. No. 16/227,287, filed Dec. 20, 2018, which is a continuation of U.S. patent application Ser. No. 15/988,628, filed May 24, 2018, which is a continuation of U.S. patent application Ser. No. 15/728,872, filed Oct. 10, 2017, which is a continuation of U.S. patent application Ser. No. 14/209,480, filed Mar. 13, 2014, which is a continuation of U.S. patent application Ser. No. 11/576,871, filed Jan. 30, 2009, which is a U.S. National Stage under 35 U.S.C. § 371 of International Application No. PCT/DK2005/00648, filed Oct. 7, 2005, which claims benefit of U.S. Provisional Application No. 60/691,513, filed Jun. 16, 2005. U.S. patent application Ser. No. 16/227,287 is hereby incorporated by reference herein in its entirety.

FIELD OF THE INVENTION

The present invention relates to controlled release pharmaceutical compositions comprising a fumaric acid ester as an active substance. The compositions are suitable for use in the treatment of e.g. psoriasis or other hyperproliferative, inflammatory or autoimmune disorders and are designed to release the fumaric acid ester in a controlled manner so that local high concentrations of the active substance within the gastrointestinal tract upon oral administration can be avoided and, thereby, enabling a reduction in gastro-intestinal related side-effects.

BACKGROUND OF THE INVENTION

Fumaric acid esters, i.e. dimethylfumarate in combination with ethylhydrogenfumarat have been used in the treatment of psoriasis for many years. The combination is marketed under the tradename Fumaderm®. It is in the form of tablets intended for oral use and it is available in two different dosage strengths (Fumaderm® initial and Fumaderm®):

|  | Fumaderm ® Initial | Fumaderm ® |
|---|---|---|
| Dimethylfumarate | 30 mg | 120 mg |
| Ethylhydrogenfumarate, calcium salt | 67 mg | 87 mg |
| Ethylhydrogenfumarate, Magnesium salt | 5 mg | 5 mg |
| Ethylhydrogenfumarate, Zinc salt | 3 mg | 3 mg |

The two strengths are intended to be applied in an individually based dose regimen starting with Fumaderm® initial in an escalating dose, and then after e.g. three weeks of treatment switching to Fumaderm®. Both Fumaderm® initial and Fumaderm® are enteric coated tablets.

Another marketed composition is Fumaraat 120® containing 120 mg of dimethylfumarate and 95 mg of calcium monoethylfumarate (TioFarma, Oud-Beijerland, Netherlands). In a recent publication (Litjens et al. Br. J. Clin. Pharmacol. 2004-, vol. 58:4, pp. 429-432), the pharmacokinetic profile of Fumaraat 120® is described in healthy subjects. The results show that a single oral dose of Fumaraat 120® is followed by a rise in serum monomethylfumarate concentration and only negligible concentrations of dimethylfumarate and fumaric acid is observed. The results indicate that dimethylfumarate is rapidly hydrolyzed to monomethylfumarate in an alkaline environment, but according to the authors not in an acid environment. As the composition is enteric coated, it is contemplated that the uptake of fumarate takes place mainly in the small intestine, where dimethylfumarate before uptake is hydrolysed to the monoester due to an alkaline environment, or it may rapidly be converted due to esterases in the circulation. Furthermore, the study shows that $t_{max}$ and $C_{max}$ are subject to food effect, i.e. $t_{max}$ is prolonged (mean for fasted conditions is 182 min, whereas for fed conditions mean is 361 min) [lag time is 90 min for fasted and 300 min for fed] and $C_{max}$ is decreased (fasted: 0.84 mg/I, fed: 0.48 mg/l) by concomitant food-intake. Another study (Reddingius W. G. Bioanalysis and Pharmacokinetics of Fumarates in Humans. Dissertation ETH Zurich No. 12199 (1997)) in healthy subjects with two tablets of Fumaderm® P forte revealed $C_{max}$ values (determined as monoethyl- or monomethylfumarate) in a range from 1.0 to 2.4 µg/ml and a $t_{max}$ in a range of from 4.8 to 6.0 hours.

U.S. Pat. Nos. 6,277,882 and 6,355,676 disclose respectively the use of alkyl hydrogen fumarates and the use of certain fumaric acid mono alkyl ester salts for preparing micro tablets for treating psoriasis, psoriatic arthritis, neurodermatitis and enteritis regionalis Crohn. U.S. Pat. No. 6,509,376 discloses the use of certain dialkyl fumarates for the preparation of pharmaceutical preparations for use in transplantation medicine or the therapy of autoimmune diseases in the form of micro tablets or pellets. U.S. Pat. No. 4,959,389 disclose compositions containing different salts of fumaric acid monoalkyl ester alone or in combination with dialkyl fumarate. GB 1,153,927 relates to medical compositions comprising dimethylmaleic anhydride and/or dimethylmaleic acid and/or a dimethylfumaric acid compounds. The Case report "Treatment of disseminated granuloma annulare with fumaric acid esters" from BMC Dermatology, vol. 2, no. 5, 2002, relates to treatment with fumaric acid esters.

However, therapy with fumarates like e.g. Fumaderm® frequently gives rise to gastro-intestinal side effects such as e.g. fullness, diarrhea, upper abdominal cramps, flatulence and nausea.

Accordingly, there is a need to develop compositions comprising one or more therapeutically or prophylactically active fumaric acid esters that provide an improved treatment with a reduction in gastro-intestinal related side effects upon oral administration.

Furthermore, the present commercially available products contain a combination of two different esters of which one of the esters (namely the ethylhydrogenfumarate which is the monoethylester of fumaric acid) is present in three different salt forms (i.e. the calcium, magnesium and zinc salt). Although each individual form may have its own therapeutic profile it would be advantageous to have a much simpler product, if possible, in order to obtain a suitable therapeutic effect.

The present inventors contemplate that an improved treatment regimen may be obtained by administration of a pharmaceutical composition that is designed to deliver the active substance in a controlled manner, i.e. in a manner that is prolonged, slow and/or delayed compared with the commercially available product. Furthermore, it is contemplated that instead of using a combination of different fumaric acid esters, a suitable therapeutic response may be achieved by use of a single fumaric acid ester alone such as dimethylfumaric acid.

SHORT DESCRIPTION OF THE FIGURES

DISCLOSURE OF THE INVENTION

Figure 1:
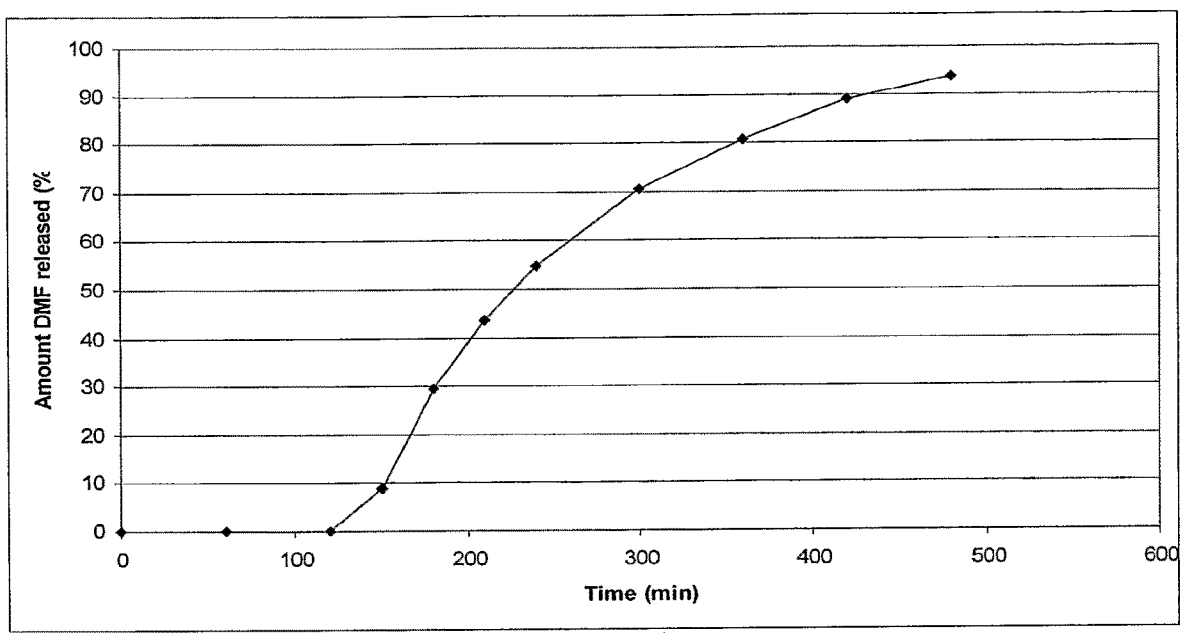
FIG. 1 shows an example of an in vitro dissolution profile of a capsule prepared as described in example 5.

Accordingly, the present invention relates to a pharmaceutical composition comprising as an active substance one or more fumaric acid esters selected from di-$(C_1$-$C_5)$alkylesters of fumaric acid and mono-$(C_1$-$C_5)$alkylesters of fumaric acid, or a pharmaceutically acceptable salt thereof, which—upon oral administration and in comparison to that obtained after oral administration of Fumaderm® tablets in an equivalent dosage—gives a reduction in GI (gastro-intestinal) related side-effects.

As mentioned above, the present inventors contemplate that a suitable way of reducing the gastro-intestinal related side-effects is by administration of the active substance in the form of a controlled release composition.

Accordingly, the present invention relates in a further aspect to a controlled release pharmaceutical composition for oral use comprising as an active substance one or more fumaric acid esters selected from di-$(C_1$-$C_5)$alkylesters of fumaric acid and mono-$(C_1$-$C_5)$alkylesters of fumaric acid, or a pharmaceutically acceptable salt thereof, wherein the release of the fumaric acid ester—when subjected to an in vitro dissolution test employing 0.1N hydrochloric acid as dissolution medium during the first 2 hours of the test and then 0.05 M phosphate buffer pH 6.5 as dissolution medium—is as follows:

within the first 3 hours after start of the test at the most about 70% w/w of the total amount of the fumaric acid ester contained in the composition is released, and/or within the first 4 hours after start of the test at the most about 92% w/w of the total amount of the fumaric acid ester is released, and/or within the first 5 hours after start of the test at the most about 94% w/w of the total amount of the fumaric acid ester is released, and/or within the first 6 hours after start of the test at the most about 95% w/w of the total amount of the fumaric acid ester contained in the composition is released, and/or within the first 7 hours after start of the test at the most about 98% w/w of the total amount of the fumaric acid ester contained in the composition is released, and/or within the first 9 hours after start of the test at the most about 99% w/w of the total amount of the fumaric acid ester contained in the composition is released and/or within the first 12 hours after start of the test at the most about 99% w/w of the total amount of the fumaric acid ester contained in the composition is released.

In the present context, a controlled release composition is a composition that is designed to release the fumaric acid ester in a prolonged, slow and/or delayed manner compared to the release of the commercially available product Fumaderm®, when tested under comparable conditions (e.g. for in vivo studies: dose equivalents, with or without standardized meal etc., or for in vitro studies: dose equivalents, dissolution test apparatus and working conditions including e.g. composition, volume and temperature of dissolution medium employed, rotation speed etc.).

The release in vivo may be tested by measuring the plasma concentration at predetermined time periods and thereby obtaining a plasma concentration versus time profile for the fumaric acid ester in question or, if relevant, a metabolite thereof. (E.g. in the case of dimethylfumarate, the active substance is envisaged to be methylhydrogenfumarate, i.e. the monomethyl ester of fumaric acid). Furthermore, it is contemplated that metabolism already takes place within the gastro-intestinal tract or during passage of the gastro-intestinal mucosa, or upon first passage through the hepatic circulation. Accordingly, when dimethylfumarate is administered, the relevant component to search for in the plasma may be the monomethyl ester and not the dimethylester of fumaric acid.

Other tests may also be used to determine or to give a measure of the release of the active substance in vivo. Thus, animals (e.g. mice, rats, dogs etc.) may be used as a model. The animals receive the compositions under investigation and after specified periods of time, the animals are sacrificed and the content of the active ingredient (or metabolite thereof, if relevant) is determined in plasma or specific organs or extracted from the intestinal contents.

Another test involves the use of a specific segment of an animal intestine. The segment is placed in a suitable dissolution apparatus containing two compartments (a donor and a receiver) separated by the segment, and the composition under investigation is placed in a suitable medium in one compartment (the donor compartment). The composition will release the active substance that subsequently is transported across the intestinal segment. Accordingly, at suitable time intervals, the concentration of the active substance (or, if relevant, the metabolite) is measured in the receiver compartment.

A person skilled in the art will be able to adapt the above-mentioned method to the specific composition.

With respect to in vitro methods, well-established methods are available, especially methods described by official monographs like e.g. United States Pharmacopeia (USP) or the European Pharmacopoeia. A person skilled in the art will know which method to choose and how to select the specific conditions to carry out the in vitro test. For instance, the USP prescribes in vitro tests be carried out at 37 +/−1.0 such as 37 +/−0.5 degrees Celsius/Centigrade. A suitable dissolution test is, for example as described in example 29, for capsules, wherein the dissolution profile is determined as described in the United States Pharmacopoeia at 37° C. using a rotating basket at 100 rpm employing 0.1N hydrochloric acid as dissolution medium during the first 2 hours of the test and then followed by 0.05 M phosphate buffer pH 6.5 as dissolution medium for the remaining test period, and, for example as described in example 30, for tablets wherein the dissolution profile is determined as described in the United States Pharmacopoeia at 37° C. using a paddle dissolution apparatus at 100 rpm employing 0.1N hydrochloric acid as dissolution medium during the first 2 hours of the test and then followed by 0.05 M phosphate buffer pH 6.5 as dissolution medium for the remaining test period.

As mentioned above, the in vivo release of the active substance is prolonged, slow and/or delayed compared with the commercially available Fumaderm® composition. In the present context, the term "prolonged" is intended to indicate that the active substance is released during a longer time period than Fumaderm® such as at least during a time period that is at least 1.2 times, such as, e.g., at least 1.5 times, at least 2 times, at least 3 times, at least 4 times or at least 5 times greater than that of Fumaderm®. Thus, if e.g. 100% of dimethylfumarate is released from Fumaderm® tablets 3 hours after the start of a suitable test, then 100% of dimethylfumarate in a composition according to the invention is released at least 3.6 hours after the start of a suitable test.

In the present context the term "delayed" is intended to indicate that the release of the active substance starts at a later point in time compared with that of Fumaderm® (such as at 30 min or more later such as, e.g., 45 min or more later, 1 hour or more later or 1.5 hours or more later, alternatively, that the initial release during the first 2 hours is much less compared with that of Fumaderm® (i.e. less than 80% w/w such as, e.g., less than 70% w/w, less than 60% w/w or less than 50% of that of Fumaderm®).

As used in the present invention, a gastrointestinal (GI) side effect may include, but is not limited to diarrhea, stomach ache, stomach pain, abdominal pain, abdominal cramps, nausea, flatulence, tenesmus, meteorism, an increased frequency of stools, a feeling of fullness and upper abdominal cramps.

In the present context, a reduction of GI related side effects is intended to denote a decrease in severity and/or incidence among a given treated patient population, compared to the GI side effects observed after administration of the composition according to the invention compared with that of Fumaderm®. A reduction in GI related side effects according to this definition could thus be construed as a substantial reduction in incidence of any of the GI side effect listed above, such as at least a 10% reduction in incidence or more preferably at least 20% reduction in incidence or even more preferable a more than 30% reduction in incidence. A reduction in GI related side effect can also be expressed as a substantial reduction in severity in any of the GI side effects listed above, such as a reduction in severity and/or frequency of diarrhea, stomach ache, stomach pain, abdominal pain, abdominal cramps, nausea, flatulence, tenesmus, meteorism, increased frequency of stools, a feeling of fullness or upper abdominal cramps. The reduction of GI related side effects, as described above, can be monitored in a clinical trial setting, either comparing the administration of the composition according to the invention head on with Fumaderm® or with placebo. In case of a placebo controlled trial, the incidence of GI related side effects in the patients receiving the composition according to the invention compared to the placebo group, can be compared to historical trials comparing Fumaderm® to placebo (see e.g. Altmeyer et al, J. Am. Acad. Dermatol. 1994; full reference: Altmeyer P J et al, Antipsoriatic effect of fumaric acid derivatives. Results of a multicenter double-blind study in 100 patients. J. Am. Acad. Dermatol. 1994; 30:977-81). Typically, patients suffering from psoriasis are included in such a study, and typically more than 10% of the body surface area will be affected by psoriasis (severe psoriasis). However, patients in whom between 2 and 10 percent of the body surface area is affected can also be included (moderate psoriasis). Patients can also be selected based on the psoriasis area severity index (PASI). Typically, patients within a certain range of PASI are included, such as between 10 and 40, or such as between 12 and 30, or such as between 15 and 25. Patients with any type of psoriasis may be included (chronic plaque type, exanthematic guttate type, pustular type, psoriatic erythroderma or palmoplantar type), but in some cases only patients with the chronic plaque type are included. About 15 to 20 patients in each treatment group (composition according to the invention and Fumaderm® or placebo) are sufficient in most cases, but more preferably about 30 to 50 patients are included in each arm of the study. Total study duration can be as short as one day to one week, but more preferably the study will run for 8 weeks to 12 weeks or up to 16 weeks. The side effects can e.g. be assessed as the total number of times a certain side effect was reported in each group (irrespective of how many patients have experienced the side effect), or the side effects can be assessed as the number of patients that have experienced a certain side effect a certain number of times, such as at least once or at least twice or at least three times during the duration of the study. Furthermore, the severity of a side effect can be monitored, or a certain severity of a side effect can be required for it to qualify as a side effect in the study. A convenient way of assessing the severity of a side effect is via a visual analogue (VAS) scale.

Active Substance

The active substance in a composition of the invention is any fumaric acid ester. In one embodiment of the invention the fumaric acid ester is preferably selected from the group consisting of dimethylfumarate, diethylfumarate, dipropylfumarate, dibutylfumarate, dipentylfumarate, methyl-ethylfumarate, methyl-propylfumarate, methyl-butylfumarate, methyl-pentylfumarate, monomethylfumarate, monoethylfumarate, monopropylfumarate, monobutylfumarate and monopentylfumarate, including pharmaceutically acceptable salts thereof.

In a specific embodiment of the invention, the fumaric acid ester is a mono-$(C_1-C_5)$alkylester of fumaric acid that is present in the form of a pharmaceutically acceptable salt. Suitable salts are e.g. metal salts such as a salt selected from alkali metal salts and alkaline earth metal salts including sodium, potassium, calcium, magnesium or zinc salt.

The term $(C_1-C_5)$alkyl refers to a branched or un-branched alkyl group having from one to five carbon atoms inclusive, such as methyl, ethyl, 1-propyl, 2-propyl, 1-butyl, 2-butyl, 2-methyl-2-propyl, 2-methyl-1-propyl and pentyl.

In another embodiment, the composition according to the invention comprises dimethylfumarate as the active substance.

In a further embodiment, the composition according to the invention comprises monomethylfumarate as the active substance optionally in the form of a pharmaceutically acceptable salt like e.g. its sodium, potassium, calcium, magnesium and/or zinc salt.

In another embodiment, the composition according to the invention consists essentially of dimethylfumarate as the active substance.

In another embodiment, the composition according to the invention consists of dimethylfumarate as the active substance.

In a further embodiment, the composition according to the invention consists essentially of monomethylfumarate as the active substance optionally in the form of a pharmaceutically acceptable salt like e.g. its sodium, potassium, calcium, magnesium and/or zinc salt.

In a further embodiment, the composition according to the invention consists of monomethylfumarate as the active substance optionally in the form of a pharmaceutically acceptable salt like e.g. its sodium, potassium, calcium, magnesium and/or zinc salt.

In a further embodiment, the composition according to the invention comprises dimethylfumarate and monomethylfumarate (optionally in the form of a pharmaceutically acceptable salt like e.g. its sodium, potassium, calcium, magnesium and/or zinc salt) as the active substances, in a weight ratio between about 1:10 and about 10:1.

In a further embodiment, the composition according to the invention consists essentially of dimethylfumarate and monomethylfumarate (optionally in the form of a pharmaceutically acceptable salt like e.g. its sodium, potassium, calcium, magnesium and/or zinc salt) as the active substances, in a weight ratio between about 1:10 and about 10:1.

In a further embodiment, the composition according to the invention consists of dimethylfumarate and monomethylfumarate (optionally in the form of a pharmaceutically acceptable salt like e.g. its sodium, potassium, calcium, magnesium and/or zinc salt) as the active substances, in a weight ratio between about 1:10 and about 10:1.

Cosmetic and/or Pharmaceutical Compositions

The problem the invention solves is related to the appearance of gastro-intestinal side-effects upon oral administration of fumaric acid esters. By prolonging and/or delaying the release of the active substance from the composition it is envisaged that the local concentration of the active substance at specific sites of the gastro-intestinal tract is reduced (compared with that of Fumaderm®) which in turn leads to a reduction in gastro-intestinal side-effects. Accordingly, compositions that enable a prolonged and/or a slow release of a fumaric acid ester as defined above are within the scope of the present invention.

Such compositions are well-known to the skilled artisan and include e.g. diffusion-controlled drug delivery systems, osmotic pressure controlled drug delivery systems, erodible drug delivery systems etc. Moreover, there are pharmaceutical companies that based on a specific technology (such as mentioned above) can provide a specific composition with specific release characteristics of the active substance. Accordingly, a person skilled in the art will know how to obtain a suitable product once he has realized a specific need in respect of a particular drug substance. By way of example, Eurand is one of such companies that offer technical solutions in order to obtain a controlled release pharmaceutical composition containing a specific active substance and having specific requirements with respect to the release of the active substance from the composition (see e.g. http://www.eurand.com). Another company is MacroMed, Inc. that has developed a technology involving a so-called SQZgel™ (http://macromed.com, SQZgel™'s mechanism of action is a pH-sensitive polymer mixture combined with an outer coating. In the acidic environment of the stomach the polymer imbibes with water and swells, entrapping the drug. Upon entering the higher pH of the intestines, the polymer slowly shrinks, or "squeezes" at a "dialed-in" rate releasing the active composition in a sustained manner), or Egalet a/s that has a specific extrusion based technology (http://www.egalet.com, Key elements of the Egalet® technology are a biodegradable coat and a matrix, comprising the active drug, which is surface erodible, hydrophobic and composed of PEG-stearate. One of the Egalet® technologies is the 2K Egalet® constant release system, which is a 2-component production model consisting of coat and matrix. The drug is evenly distributed throughout the Egalet® matrix for constant release over time. Also of interest in the present context are technologies like e.g. the Eurand technologies Diffucaps (Drug release profiles are created by layering active drug onto a neutral core such as sugar spheres, crystals or granules followed by a rate-controlling, functional membrane. Diffucaps/Surecaps beads are small in size, approximately 1 mm or less in diameter. By incorporating beads of differing drug release profiles into hard gelatin capsules, combination release profiles can be achieved), Diffutabs (The Diffutab technology incorporates a blend of hydrophilic polymers that control drug release through diffusion and erosion of a matrix tablet), Minitabs (Eurand Minitabs are tiny (2 mm×2 mm) tablets containing gel-forming excipients that control drug release rate. Additional membranes may be added to further control release rate), Orbexa (This technology produces beads that are of controlled size and density with a defined-based granulation extrusion and spheronization techniques. The resultant beads can be coated with release rate controlling membranes for additional release rate control and may be filled into capsules or provided in sachet form) and SDS (Eurand's SDS technology uses functional polymers or a combination of functional polymers and specific additives, such as composite polymeric materials, to deliver a drug to a site of optimal absorption along the intestinal tract. In order to achieve this, Eurand first produces multiparticulate dosage forms such as Diffucaps or Eurand Minitabs, which incorporate the active drug. These dosage forms are then coated with pH dependent/independent polymeric membranes that will deliver the drug to the desired site. These are then filled into hard gelatin capsules).

Another interesting technology for use in formulating compositions according to the present invention is the so-called MeltDose® technology as described in WO 03/004001 (see http://www.lifecyclepharma.conn. MeltDose® involves formulating solubilized, individual molecules into tablets. By formulating individual molecules, the primary limitation of oral absorption of drugs with low water-solubility is removed, and a superior bioavailability can be attained). By employing this technology it is possible to obtain a particulate material that is suitable for processing into various pharmaceutical dosage forms e.g. in the form of pellets or tablets. Furthermore, the technology is suitable for use as it is possible to obtain a suitable release profile of the active substance, e.g. such as those release profiles described herein. In one embodiment, pellets suitable for use may have a mean particle size larger than 2000 µm. In another embodiment, pellets suitable for use may have a mean particle size of from about 0.01 µm to about 250 µm.

Another specific suitable formulation principle for use in the present context is formulation in a lipophilic environment such as, e.g., soft gelatin capsules. A suitable example of this formulation principle is Vegicaps Soft from Scherer (a soft capsule technology based on carrageenan and starch, which despite being 100% plant-derived, still offers all the key attributes of traditional soft gelatin capsules. These include a soft and flexible dosage form that provides ease of swallowing_) (For further information see http://www.rp-scherer.de/page.php?pageID=94).

A further specific example of a suitable formulation comprises the formulation of the active substance together with Vitamin E concentrate in soft or hard gelatin capsules. This formulation, in a modified form, is the basis of the commercial cyclosporine product, Neoral®, containing, among other things, corn oil-mono-di-triglycerides, polyoxyl 40 hydrogenated castor oil NF, DL-α-tocopherol USP (part of the vitamin E family), gelatin NF, glycerol, iron oxide black, propylene glycol USP, titanium dioxide USP, carmine, and alcohol in addition to cyclosporine.

Another specific example of a suitable formulation comprises the formulation of active substance together with ethanol, tocopherolethylene glycol 1000 succinate (TPGS), corn oil and wax in soft or hard gelatin capsules. This product can be a semi-solid or solid dosage form. The release rate of this formulation is dependent on degradation due to lipases in the intestine.

A further example of a suitable formulation comprises the formulation of the active substance together with ethanol, tocopherolethylene glycol 1000 succinate (TPGS), corn oil and polyglycolized glycerides (e.g. Gelucire) in soft or hard gelatin capsules. This product can be a semi-solid or solid dosage form. The release rate of this formulation is dependent on degradation due to lipases in the intestine.

A further example of a suitable formulation is an oral pulsed dose drug delivery system. This dosage form can be perceived as a modified form of the Schering Repetab tablets. A portion of the composition of the present invention is put in the core of a tablet.

The core can for example be made by conventional wet granulation or continuous granulation such as extrusion followed by compaction of the granulate into tablets. The core is then coated using an appropriate technology, preferably by airsuspension using an enteric coating polymer such as Eudragits.

The first releasing dose is compression coated on the core or air-suspension coated either with the enteric coat or on top of the enteric coat. In a embodiment of the invention, the first releasing dose is air-suspension coated with the enteric coat. In a further embodiment of the invention, the first releasing dose is compression coated on the core, in order to avoid release of the composition according to the invention prior to the degradation of the enteric coat, such degradation typically occurring at pH values higher than those found in the gastric ventricle; i.e. the degradation of the enteric coat typically occurs after passage of the gastric ventricle.

A further example of a suitable formulation is an oral sustained drug delivery system. A portion of the composition of the present invention is put in the core of a tablet.

The core can for example be made by conventional wet granulation or continuous granulation such as extrusion followed by compaction of the granulate into tablets. The core is coated using an appropriate technology, preferably by alrsuspension using ethylcellulose and a hydrophilic excipient such as hydroxyl propyl cellulose (HPC).

The first releasing dose is compression coated on the core or air-suspension coated either with the enteric coat or on top of the enteric coat. In a preferred embodiment of the invention, the first releasing dose is air-suspension coated with the enteric coat. In a further embodiment of the invention, the first releasing dose is compression coated on the core, in order to avoid release of the composition according to the invention prior to the degradation of the enteric coat, such degradation typically occurring at pH values higher than those found in the gastric ventricle; i.e. the degradation of the enteric coat typically occurs after passage of the gastric ventricle.

A further example of a suitable formulation is obtained via crystal engineering, such as e.g. described in WO 03/080034, which is hereby incorporated by reference.

Accordingly, in another embodiment the composition of the invention comprises the active substance in the form of micro-crystals with hydrophilic surfaces. Furthermore, in another embodiment of the invention, the micro-crystals are filmcoated directly, in order to achieve a sustained release formulation.

Another specific example of a suitable formulation comprises complexation of the composition according to the present invention with genuine cyclodextrins and cyclodextrin-derivatives (e.g. alkyl- and hydroxyalkyl-derivatives or sulfobutyl-derivatives). The complexation is achieved in accordance with well known methods. It is contemplated that such a complexation leads to a higher solubility and a higher dissolution rate of the composition according to the invention, compared to the composition prior to complexation. Furthermore, it is contemplated that such a complexation leads to a higher bioavailability of the composition according to the invention, compared to the composition prior to complexation.

In specific embodiments, the invention relates to a controlled release pharmaceutical composition that may be administered one, two or more times daily, such as once or twice or three times daily. Furthermore, the composition may be designed so that it releases the fumaric acid ester relatively independent on pH, i.e. the release is not dependent on pH in the gastrointestinal tract. Examples of such compositions are e.g. compositions in the form of solid dosages forms (e.g. tablets, capsules, pellets, beads etc.) that are coated with a controlled release coating. Suitable materials for controlled release coatings are e.g. cellulose and cellulose derivatives including methylcellulose, ethylcellulose and cellulose acetate, or poly(ethylene-co-vinyl acetate), poly (vinyl chloride).

The release of the fumaric acid ester typically takes place in three steps from a composition coated with a diffusion controlled membrane:

i) firstly, water (from the GI tract) diffuses into the dosage form from the surroundings, ii) secondly, at least some of the fumaric acid ester present in the dosage form dissolves by the action of water, iii) the dissolved fumaric acid ester diffuses out of the dosage form and into the surroundings (i.e. the GI tract)

Other examples include e.g. matrix tablets or dosage form containing a multiplicity of units each in the form of a matrix system. The active substance is embedded in a matrix containing e.g. cellulose and cellulose derivatives including microcrystalline cellulose, hydroxypropyl methyl cellulose, hydroxypropyl cellulose and methylcellulose, povidone, poly(ethyleneoxide) (PEO), polyethylene glycol (PEG), poly (vinyl alcohol) (PVA), xanthan gum, carrageenan and other synthetic materials. Substances normally used as pharmaceutically acceptable excipients or additives may be added to a matrix composition.

Other examples of suitable compositions are e.g. hydrogels, i.e. monolithic systems wherein the active substance is embedded in a water-swellable network polymer. Materials suitable for use include e.g. hydrophilic vinyl and acrylic polymers, polysaccharides like alginates, and poly(ethylene oxide).

In specific embodiments, a composition according to the invention has a pH controlled release (also known as a pH dependent release) of the fumaric acid ester. Normally, the release is designed so that only a small amount, if any, of the fumaric acid ester is released in the stomach (pH up to about 3), whereas the fumaric acid ester is released in the intestines (pH shifts to about 6-7). Such a pH controlled release can be obtained by providing a composition of the invention with an enteric coating (the whole composition or, if the composition is a multiparticulate composition, the individual units) or by providing a composition that releases the fumaric acid by a pH-dependent osmotic mechanism, or by employment of suitable enzymes.

Examples of suitable substances for use as enteric coating materials include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, poly acrylic methacrylic acid copolymers, shellac and vinyl acetate and crotonic acid copolymers, etc.

The compositions mentioned above having a pH independent release may also be formulated to release the fumaric acid ester e.g. by providing the composition with an outer layer of an enteric coating.

Furthermore, the compositions may be formulated in such a manner that an initial delay in release of the fumaric acid ester is obtained. Such a delay may be obtained e.g. by choosing an outermost coating that in a time-controlled manner degrades (e.g. erodes) and only when this outermost coating is eroded away, the release of the fumaric acid ester starts.

In the following is given a description of various compositions according to the invention that are designed to obtain a suitable release of the fumaric acid ester. Based on the description above and handbooks within the field of controlled release of pharmaceutics, a person skilled in the art will know how to choose different formulation principles in order to achieve the required release profile.

Compositions Designed to be Administered Two or More Times Daily pH Independent Release In the following is given a description of specific embodiments, wherein the fumaric acid ester is released independently of pH and wherein the release pattern is suitable for compositions that are administered two or more times daily. Examples of suitable formulation principles are e.g. compositions provided with a diffusion coating such as a controlled release diffusion coating, matrix particulates or matrix tablets, hydrogels, pulsed dose drug delivery systems, co-formulation with vitamin E concentrate or ethanol, TPGS, corn oil and wax etc., including any of the formulation principles mentioned above.

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test employing water as dissolution medium—is as follows:

within the first 6 hours after start of the test at the most about 60% w/w such as, e.g., from about 30% to about 60% w/w, from about 40% to about 55% w/w, or about 50% of the total amount of the fumaric acid ester contained in the composition is released, and/or within the first 9 hours after start of the test at the most about 85% w/w such as, e.g., from about 50% to about 85% w/w, from about 60% to about 80% w/w, or about 75% of the total amount of the fumaric acid ester contained in the composition is released, and/or within the first 12 hours after start of the test at least about 80% w/w such as, e.g., about 80% w/w or more, about 85% w/w or more, about 90% w/w or more or about 95% w/w or more of the total amount of the fumaric acid ester contained in the composition is released, and/or the total amount of the fumaric acid ester contained in the composition is released within the first 12 hours after start of the test.

pH Controlled Release

In the following is given a description of specific embodiments, wherein the fumaric acid ester is released depending on pH and wherein the release pattern is suitable for compositions that are administered two or more times daily. Examples of suitable formulation principles are e.g. compositions provided with an enteric coating or hydrogels of a type described by Zentner et al (U.S. Pat. No. 6,537,584) and Bae (U.S. Pat. No. 5,484,610), which hereby are incorporated by reference. Further examples of suitable formulation principles are e.g. compositions provided with a diffusion coating such as a controlled release diffusion coating, matrix particulates or matrix tablets, hydrogels, pulsed dose drug delivery systems, co-formulation with vitamin E concentrate or ethanol, TPGS, corn oil and wax etc., including any of the formulation principles mentioned above, optionally with an enteric coating.

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test employing 0.1N hydrochloric acid as dissolution medium during the first 2 hours of the test and then 0.05 M phosphate buffer pH 6.5 or 6.8 as dissolution medium—is as follows:

within the first 2 hours after start of the test at least about 1% w/w such as, e.g. at least about 2% w/w, at least about 3% w/w, or about 5% w/w of the total amount of the fumaric acid ester is released, and/or within the first 3 hours after start of the test at the most about 35% w/w such as, e.g., from about 15% to about 35% w/w, from about 20% to about 30% w/w, or about 25% w/w of the total amount of the fumaric acid ester is released, and/or within the first 3 hours after start of the test from about 10% to about 70% w/w, from about 10% to about 65% w/w, from about 10% to about 60% w/w, from about 15% to about 50% w/w, from about 15% to about 35% w/w, from about 20% to about 30% w/w, or about 20% w/w, or about 25% w/w of the total amount of the fumaric acid ester is released, and/or within the first 4 hours after start of the test at the most about 92% w/w such as, e.g., from about 10% to about 92% w/w, from about 20% to about 85% w/w, from about 20% to about 80% w/w, from about 20% to about 70% w/w, from about 25% to about 60% w/w, from about 25% to about 55% w/w, from about 30% to about 50% w/w, or about 35% w/w, or about 40% w/w, or about 45% w/w of the total amount of the fumaric acid ester is released, and/or within the first 5 hours after start of the test at the most about 94% w/w such as, e.g., from about 15% to about 94% w/w, from about 25% to about 90% w/w, from about 30% to about 85% w/w, from about 35% to about 80% w/w, from about 35% to about 75% w/w, from about 40% to about 70% w/w, from about 45% to about 70% w/w, from about 55% to about 70% w/w, from about 60% to about 70% w/w, or about 45% w/w, or about 50% w/w, or about 55% w/w, or about 60% w/w, or about 65% w/w of the total amount of the fumaric acid ester is released, and/or within the first 6 hours after start of the test at the most about 60% w/w such as, e.g., from about 30% to about 60% w/w, from about 40% to about 55% w/w, or about 50% w/w of the total amount of the fumaric acid ester contained in the composition is released, and/or within the first 6 hours after start of the test at the most about 95% w/w such as, e.g., from about 35% to about 95% w/w, from about 40% to about 90% w/w, from about 45% to about 85% w/w, from about 50% to about 85% w/w, from about 55% to about 85% w/w, from about 60% to about 85% w/w, from about 65% to about 85% w/w, from about 70% to about 85% w/w, from about 75% to about 85% w/w, or about 65% w/w, or about 70% w/w, or about 75% w/w, or about 80% w/w of the total amount of the fumaric acid ester contained in the composition is released, and/or within the first 7 hours after start of the test at the most about 98% w/w such as, e.g., from about 45% to about 98% w/w, from about 50% to about 98% w/w, from about 55% to about 98% w/w, from about 60% to about 98% w/w, from about 65% to about 98% w/w, from about 70% to about 98% w/w, from about 75% to about 95% w/w, from about 80% to about 95% w/w, from about 85% to about 95% w/w, or about 75% w/w, or about 80% w/w, or about 85% w/w, or about 90% w/w of the total amount of the fumaric acid ester contained in the composition is released, and/or within the first 9 hours after start of the test at the most about 85% w/w such as, e.g., from about 50% to about 85% w/w, from about 60% to about 80% w/w, or about 75% w/w of the total amount of the fumaric acid ester contained in the composition is released, and/or within the first 9 hours after start of the test at the most about 99% w/w such as, e.g., from about 60% to about 99% w/w, from about 70% to about 99% w/w, from about 80% to about 99% w/w, from about 90% to about 99% w/w, or about 95% w/w of the total amount of the fumaric acid ester contained in the composition is released.

In another aspect of the invention a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, characterized in that it consists of a controlled-release dosage form adapted to release di-($C_1$-$C_5$)alkylester and/or a mono-($C_1$-$C_5$)alkylester of fumaric acid or a pharmaceutically acceptable salt thereof over a predetermined time period, according to a in vitro profile of dissolution when measured according to USP in 0.1N hydrochloric acid during the first 2 hours and then 0.05 M phosphate buffer at a pH 6.5 or 6.8, wherein at the most 5% w/w of the total amount of the fumaric acid ester contained in the composition is released within the first 2 hours after start of the test, and/or wherein from about 20% to about 75% w/w of the total amount of the fumaric acid ester contained in the composition is released within the first 3 hours after start of the test, and/or wherein from about 50% to about 90% w/w of the total amount of the fumaric acid ester contained in the composition is released within the first 4 hours after start of the test, and/or wherein from about 60% to about 90% w/w of the total amount of the fumaric acid ester contained in the composition is released within the first 5 hours after start of the test, and/or wherein from about 70% to about 95% w/w of the total amount of the fumaric acid ester contained in the composition is released within the first 6 hours after start of the test, and/or wherein from about 75% to about 97% w/w of the total amount of the fumaric acid ester contained in the composition is released within the first 7 hours after start of the test, is provided.

In a further aspect of the invention a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, characterized in that it consists of a controlled-release dosage form adapted to release di-($C_1$-$C_5$)alkylester and/or a mono-($C_1$-$C_5$)alkylester of fumaric acid or a pharmaceutically acceptable salt thereof over a predetermined time period, according to a in vitro profile of dissolution when measured according to USP in 0.1N hydrochloric acid during the first 2 hours and then 0.05 M phosphate buffer at a pH 6.5 or 6.8, wherein at the most 5% w/w of the total amount of the fumaric acid ester contained in the composition is released within the first 2 hours after start of the test, wherein from about 20% to about 75% w/w of the total amount of the fumaric acid ester contained in the composition is released within the first 3 hours after start of the test, wherein from about 50% to about 90% w/w of the total amount of the fumaric acid ester contained in the composition is released within the first 4 hours after start of the test, wherein from about 60% to about 90% w/w of the total amount of the fumaric acid ester contained in the composition is released within the first 5 hours after start of the test, wherein from about 70% to about 95% w/w of the total amount of the fumaric acid ester contained in the composition is released within the first 6 hours after start of the test, wherein from about 75% to about 97% w/w of the total amount of the fumaric acid ester contained in the composition is released within the first 7 hours after start of the test, and wherein at least 85% w/w of the total amount of the fumaric acid ester contained in the composition is released within the first 8 hours after start of the test, is provided.

In another further aspect of the invention a controlled release pharmaceutical composition comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, characterized in that it consists of a controlled-release dosage form adapted to release di-($C_1$-$C_5$)alkylester and/or a mono-($C_1$-$C_5$)alkylester of fumaric acid or a pharmaceutically acceptable salt thereof over a predetermined time period, according to a in vitro profile of dissolution when measured according to USP in 0.1N hydrochloric acid during the first 2 hours and then 0.05 M phosphate buffer at a pH 6.5 or 6.8, wherein at the most 5% w/w of the total amount of the fumaric acid ester contained in the composition is released within the first 2 hours after start of the test and/or, wherein from about 20% to about 50% w/w of the total amount of the fumaric acid ester contained in the composition is released within the first 3 hours after start of the test, and/or wherein from about 45% to about 70% w/w of the total amount of the fumaric acid ester contained in the composition is released within the first 4 hours after start of the test, and/or wherein from about 65% to about 85% w/w of the total amount of the fumaric acid ester contained in the composition is released within the first 5 hours after start of the test, and/or wherein from about 75% to about 90% w/w of the total amount of the fumaric acid ester contained in the composition is released within the first 6 hours after start of the test, is provided.

In yet another aspect of the invention a controlled release pharmaceutical composition comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, characterized in that it consists of a controlled-release dosage form adapted to release di-($C_1$-$C_5$)alkylester and/or a mono-($C_1$-$C_5$)alkylester of fumaric acid or a pharmaceutically acceptable salt thereof over a predetermined time period, according to a in vitro profile of dissolution when measured according to USP in 0.1N hydrochloric acid during the first 2 hours and then 0.05 M phosphate buffer at a pH 6.5 or 6.8, wherein at the most 5% w/w of the total amount of the fumaric acid ester contained in the composition is released within the first 2 hours after start of the test, wherein from about 20% to about 50% w/w of the total amount of the fumaric acid ester contained in the composition is released within the first 3 hours after start of the test, wherein from about 45% to about 70% w/w of the total amount of the fumaric acid ester contained in the composition is released within the first 4 hours after start of the test, wherein from about 65% to about 85% w/w of the total amount of the fumaric acid ester contained in the composition is released within the first 5 hours after start of the test, wherein from about 75% to about 90% w/w of the total amount of the fumaric acid ester contained in the composition is released within the first 6 hours after start of the test, and wherein at least 80% of the total amount of the fumaric acid ester contained in the composition is released within the first 7 hours after start of the test, is provided.

In yet another aspect of the invention a controlled release pharmaceutical composition comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, characterized in that it consists of a controlled-release dosage form adapted to release di-($C_1$-$C_5$)alkylester and/or a mono-($C_1$-$C_5$)alkylester of fumaric acid or a pharmaceutically acceptable salt thereof over a predetermined time period, according to a in vitro profile of dissolution when measured according to USP in 0.1N hydrochloric acid during the first 2 hours and then 0.05 M phosphate buffer at a pH 6.5 or 6.8, wherein at the most 5% w/w of the total amount of the fumaric acid ester contained in the composition is released within the first 2 hours after start of the test, and/or wherein from about 50% to about 75% w/w of the total amount of the fumaric acid ester contained in the composition is released within the first 3 hours after start of the test, and/or wherein from about 70% to about 90% w/w of the total amount of the fumaric acid ester contained in the composition is released within the first 4 hours after start of the test, and/or wherein from about 80% to about 90% w/w of the total amount of the fumaric acid ester contained in the composition is released within the first 5 hours after start of the test, is provided.

In yet another aspect of the invention a controlled release pharmaceutical composition comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, characterized in that it consists of a controlled-release dosage form adapted to release di-($C_1$-$C_5$)alkylester and/or a mono-($C_1$-$C_5$)alkylester of fumaric acid or a pharmaceutically acceptable salt thereof over a predetermined time period, according to a in vitro profile of dissolution when measured according to USP in 0.1N hydrochloric acid during the first 2 hours and then 0.05 M phosphate buffer at a pH 6.5 or 6.8, wherein at the most 5% w/w of the total amount of the fumaric acid ester contained in the composition is released within the first 2 hours after start of the test, wherein from about 50% to about 75% w/w of the total amount of the fumaric acid ester contained in the composition is released within the first 3 hours after start of the test, wherein from about 70% to about 90% w/w of the total amount of the fumaric acid ester contained in the composition is released within the first 4 hours after start of the test, wherein from about 80% to about 90% w/w of the total amount of the fumaric acid ester contained in the composition is released within the first 5 hours after start of the test and wherein from about at least 90% w/w of the total amount of the fumaric acid ester contained in the composition is released within the first 6 hours after start of the test, is provided.

Release Over Gradually Shifting pH ("Half-Change" Method)

In the following is given a description of specific embodiments, wherein the fumaric acid ester is released depending on pH and wherein the release pattern is suitable for compositions that are administered two or more times daily. Examples of suitable formulation principles are e.g. compositions provided with an enteric coating or hydrogels of a type described by Zentner et al (U.S. Pat. No. 6,537,584) and Bae (U.S. Pat. No. 5,484,610), which hereby are incorporated by reference. Further examples of suitable formulation principles are e.g. compositions provided with a diffusion coating such as a controlled release diffusion coating, matrix particulates or matrix tablets, hydrogels, pulsed dose drug delivery systems, co-formulation with vitamin E concentrate or ethanol, TPGS, corn oil and wax etc., including any of the formulation principles mentioned above, optionally with an enteric coating.

The "half-change" method has specifically been developed for enteric-coated or sustained release preparations. This method encompasses hourly replacing half of the dissolution medium by an aliquot of neutral dissolution medium (to simulate the GI passage with respect to the slightly shifting pH values from duodenum to ileum). The approach is described in the following table:

| Time from start (hours) | Ratio of simulated gastric fluid/simulated intestinal fluid (%) | pH value |
| --- | --- | --- |
| 0-1 | 100/0 | 1.3 |
| 1-2 | 50/50 | 2.4 |
| 2-3 | 25/75 | 6.2 |
| 3-4 | 12.5/87.5 | 6.8 |
| 4-5 | 6.25/93.75 | 7.1 |
| 5-6 | ~3/97 | 7.2 |
| 6-7 | ~1/99 | 7.3 |
| 7-8 | ~0/100 | 7.3 |

The composition of the simulated gastric fluid can e.g. be found in the United States Pharmacopeia (USP) 2005:

2.0 g of NaCl and 3.2 g of purified pepsin, derived from porcine gastric mucosa, with an activity of 800 to 2500 units per mg of protein, is dissolved in 7.0 mL of hydrochloric acid and sufficient water to make 1000 mL. The resulting test solution has a pH of about 1.2.

Another composition of the simulated gastric fluid is found in the German E DIN 19738 (Deutsche Industrie Norm):

100 mL of synthetic/simulated gastric fluid contains 290 mg of NaCl, 70 mg of KCl, 27 mg of $KH_2PO_4$ and enough HCl to adjust the pH to 2.0. In addition, it contains 100 mg pepsin and 300 mg of mucin.

The composition of the simulated intestinal fluid can e.g. be found in the United States Pharmacopeia (USP) 2005:

6.8 g of monobasic potassium phosphate is dissolved in 250 mL of water. Mix and add 77 mL of 0.2N sodium hydroxide and 500 mL of water. 10.0 g of pancreatin is added, the solution is mixed and adjusted to a pH of 6.8±0.1 by adding either 0.2N sodium hydroxide or 0.2N hydrochloric acid. The resulting solution is diluted with water to 1000 mL.

Another composition of the simulated intestinal fluid is found in the German E DIN 19738 (Deutsche Industrie Norm):

100 mL of synthetic/simulated intestinal fluid contains 30 mg of KCl, 50 mg of $CaCl_2$, 20 mg of $MgCl_2$ and sufficient $NaHCO_3$ to adjust the pH to 7.5. Furthermore, it contains 30 mg of trypsin, 900 mg of pancreatin, 900 mg of lyophilized bile and 30 mg of urea.

In a preferred embodiment of the present invention, the "half-change" method is carried out with the simulated gastric fluid and the simulated intestinal fluid as defined by the USP 2005.

In another embodiment of the present invention, the "half-change" method is carried out with the simulated gastric fluid and the simulated intestinal fluid as defined by the USP 2005, but without the proteins (i.e. without the pepsin in the simulated gastric fluid, and without the pancreatin in the simulated intestinal fluid).

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test according to the "half-change" method—is as follows:

within the first 3 hours after start of the test from about 20% to about 40% w/w, from about 20% to about 35% w/w, or about 30% w/w of the total amount of the fumaric acid ester is released, and/or within the first 3 hours after start of the test at least about 12% w/w such as, e.g., from about 12% to about 50% w/w, from about 15% to about 45% w/vv, from about 20% to about 40% w/w, from about 20% to about 35% w/w, from about 22% to about 35% w/w, or about 25% w/w, or about 30% w/w of the total amount of the fumaric acid ester is released, and/or within the first 4 hours after start of the test from about 25% to about 40% w/w, from about 30% to about 40% w/w, or about 40% w/w of the total amount of the fumaric acid ester is released, and/or within the first 4 hours after start of the test at least about 76% w/w such as, e.g., from about 76% to about 95% w/w, from about 80% to about 90% w/w, or about 80% w/w, or about 85% w/w of the total amount of the fumaric acid ester is released, and/or within the first 4 hours after start of the test at the most about 40% w/w such as, e.g., from about 10% to about 40% w/w, from about 15% to about 35% w/w, from about 20% to about 30% w/w, or about 25% w/w, or about 30% w/w of the total amount of the fumaric acid ester is released, and/or within the first 6 hours after start of the test at least about 81% w/w such as, e.g., from about 81% to about 96% w/w, from about 85% to about 95% w/w, from about 85% to about 90% w/w, or about 80% w/w, or about 85% w/w, or about 90% w/w of the total amount of the fumaric acid ester contained in the composition is released, and/or within the first 6 hours after start of the test at the most about 50% w/w such as, e.g., from about 20% to about 50% w/w, from about 25% to about 45% w/w, from about 30% to about 45% w/w, or about 40% w/w, or about 45% w/w of the total amount of the fumaric acid ester contained in the composition is released, and/or within the first 7 hours after start of the test at least about 82% w/w such as, e.g., from about 82% to about 99% w/w, from about 85% to about 99% w/w, from about 85% to about 95% w/w, or about 90% w/w of the total amount of the fumaric acid ester contained in the composition is released, and/or within the first 7 hours after start of the test at the most about 65% w/w such as, e.g., from about 25% to about 65% w/w, from about 30% to about 65% w/w, from about 35% to about 60% w/w, from about 40% to about 60% w/w, from about 50% to about 60% w/w, or about 55% w/w, or about 60% w/w of the total amount of the fumaric acid ester contained in the composition is released, and/or within the first 8 hours after start of the test at the most about 85% w/w such as, e.g., from about 50% to about 85% w/w, from about 60% to about 80% w/w, or about 75% w/w of the total amount of the fumaric acid ester contained in the composition is released, and/or within the first 8 hours after start of the test at the most about 92% w/w such as, e.g., from about 30% to about 92% w/w, from about 35% to about 90% w/w, from about 40% to about 85% w/w, from about 45% to about 80% w/w, from about 50% to about 75% w/w, from about 55% to about 75% w/w, from about 60% to about 75% w/w, or about 65% w/w, or about 70% w/w of the total amount of the fumaric acid ester contained in the composition is released, and/or within the first 12 hours after start of the test at least about 80% w/w such as, e.g., about 80% w/w or more, about 85% w/w or more, about 90% w/w or more or about 95% w/w or more of the total amount of the fumaric acid ester contained in the composition is released.

Slow Release

In the following is given a description of specific embodiments, wherein the fumaric acid ester is released in a slow or delayed manner wherein the release pattern is suitable for compositions that are administered two or more times daily. Examples of suitable formulation principles are any of those described above.

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test employing water as dissolution medium—is as follows:

within the first 6 hours after start of the test at the most about 35% w/w such as, e.g., from about 15% to about 35% w/w such as, e.g., from about 20% to about 30% w/w, or about 25% w/w of the total amount of the fumaric acid ester contained in the composition is released, and/or within the first 8 hours after start of the test at the most about 60% w/w such as, e.g., from about 30% to about 60% w/w such as, e.g., from about 40% to about 55% w/w, or about 50% w/w of the total amount of the fumaric acid ester contained in the composition is released, and/or within the first 10 hours after start of the test at the most about 85% w/w such as, e.g., from about 50% to about 85% w/w such as, e.g., from about 60% to about 80% w/w, or about 75% w/w of the total amount of the fumaric acid ester contained in the composition is released, and/or within the first 12 hours after start of the test at least about 80% w/w such as, e.g., about 80% w/w or more such as, e.g., about 85% w/w or more, about 90% w/w or more or about 95% w/w or more of the total amount of the fumaric acid ester contained in the composition is released.

Compositions Designed to be Administered Once Daily pH Independent Release

In the following is given a description of specific embodiments, wherein the fumaric acid ester is released independent of pH and wherein the release pattern is suitable for compositions that are administered once daily. Examples of suitable formulation principles are e.g. compositions provided with a diffusion coating such as a controlled release diffusion coating, matrix particulates or matrix tablets, hydrogels, pulsed dose drug delivery systems, co-formulation with vitamin E concentrate or ethanol, TPGS, corn oil and wax etc., including any of the formulation principles mentioned above.

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test employing water as dissolution medium—is as follows:

within the first 9 hours after start of the test at the most about 60% w/w such as, e.g., from about 30% to about 60% w/w, from about 40% to about 55% w/w, or about 50% w/w of the total amount of the fumaric acid ester contained in the composition is released, and/or within the first 13.5 hours after start of the test at the most about 85% w/w such as, e.g., from about 50% to about 85% w/w, from about 60% to about 80% w/w, or about 75% w/w of the total amount of the fumaric acid ester contained in the composition is released, and/or within the first 18 hours after start of the test at least about 80% w/w such as, e.g., about 80% w/w or more, about 85% w/w or more, about 90% w/w or more or about 95% w/w or more of the total amount of the fumaric acid ester contained in the composition is released, and/or the total amount of the fumaric acid ester contained in the composition is released within the first 18 hours after start of the test.

pH Controlled Release

In the following is given a description of specific embodiments, wherein the fumaric acid ester is released dependently of pH and wherein the release pattern is suitable for compositions that are administered once daily. Examples of suitable formulation principles are e.g. compositions provided with an enteric coating or hydrogels of a type described by Zentner et al (U.S. Pat. No. 6,537,584) and Bae (U.S. Pat. No. 5,484,610). Further examples of suitable formulation principles are e.g. compositions provided with a diffusion coating such as a controlled release diffusion coating, matrix particulates or matrix tablets, hydrogels, pulsed dose drug delivery systems, co-formulation with vitamin E concentrate or ethanol, TPGS, corn oil and wax etc., including any of the formulation principles mentioned above, optionally with an enteric coating.

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test employing 0.1N hydrochloric acid as dissolution medium during the first 2 hours of the test and then 0.05 M phosphate buffer pH 6.5 or 6.8 as dissolution medium—is as follows:

within the first 2 hours after start of the test at least about 1% w/w such as, e.g. at least about 2% w/w, at least about 3% w/w, or about 5% w/w of the total amount of the fumaric acid ester is released, and/or within the first 4 hours after start of the test at the most about 90% w/w such as, e.g., from about 5% to about 90% w/w, from about 5% to about 85% w/w, from about 10% to about 80% w/w, from about 10% to about 70% w/w, from about 10% to about 65% w/w, from about 10% to about 60% w/w, from about 15% to about 50% w/w, from about 15% to about 35% w/w, from about 20% to about 30% w/w, or about 20% w/w, or about 25% w/w of the total amount of the fumaric acid ester is released, and/or within the first 4.5 hours after start of the test at the most about 35% w/w such as, e.g., from about 15% to about 35% w/w, from about 20% to about 30% w/w, or about 25% w/w of the total amount of the fumaric acid ester is released, and/or within the first 5 hours after start of the test at the most about 92% w/w such as, e.g., from about 10% to about 92% w/w, from about 20% to about 85% w/w, from about 20% to about 80% w/w, from about 20% to about 70% w/w, from about 25% to about 60% w/w, from about 25% to about 55% w/w, from about 30% to about 50% w/w, or about 35% w/w, or about 40% w/w, or about 45% w/w of the total amount of the fumaric acid ester is released, and/or within the first 6 hours after start of the test at the most about 94% w/w such as, e.g., from about 15% to about 94% w/w, from about 25% to about 90% w/w, from about 30% to about 85% w/w, from about 35% to about 80% w/w, from about 35% to about 75% w/w, from about 40% to about 70% w/w, from about 45% to about 70% w/w, from about 55% to about 70% w/w, from about 60% to about 70% w/w, or about 45% w/w, or about 50% w/w, or about 55% w/w, or about 60% w/w, or about 65% w/w of the total amount of the fumaric acid ester is released, and/or within the first 7 hours after start of the test at the most about 95% w/w such as, e.g., from about 35% to about 95% w/w, from about 40% to about 90% w/w, from about 45% to about 85% w/w, from about 50% to about 85% w/w, from about 55% to about 85% w/w, from about 60% to about 85% w/w, from about 65% to about 85% w/w, from about 70% to about 85% w/w, from about 75% to about 85% w/w, or about 65% w/w, or about 70% w/w, or about 75% w/w, or about 80% w/w of the total amount of the fumaric acid ester contained in the composition is released, and/or within the first 9 hours after start of the test at the most about 98% w/w such as, e.g., from about 45% to about 98% w/w, from about 50% to about 98% w/w, from about 55% to about 98% w/w, from about 60% to about 98% w/w, from about 65% to about 98% w/w, from about 70% to about 98% w/w, from about 75% to about 95% w/w, from about 80% to about 95% w/w, from about 85% to about 95% w/w, or about 75% w/w, or about 80% w/w, or about 85% w/w, or about 90% w/w of the total amount of the fumaric acid ester contained in the composition is released, and/or within the first 9 hours after start of the test at the most about 60% w/w such as, e.g., from about 30% to about 60% w/w, from about 40% to about 55% w/w, or about 50% w/w of the total amount of the fumaric acid ester contained in the composition is released, and/or within the first 12 hours after start of the test at the most about 99% w/w such as, e.g., from about 60% to about 99% w/w, from about 70% to about 99% w/w, from about 80% to about 99% w/w, from about 90% to about 99% w/w, or about 95% w/w of the total amount of the fumaric acid ester contained in the composition is released, and/or within the first 13.5 hours after start of the test at the most about 85% w/w such as, e.g., from about 50% to about 85% w/w, from about 60% to about 80% w/w, or about 75% w/w of the total amount of the fumaric acid ester contained in the composition is released.

Release Over Gradually Shifting pH ("Half-Change" Method)

In the following is given a description of specific embodiments, wherein the fumaric acid ester is released depending on pH and wherein the release pattern is suitable for compositions that are administered once daily. Examples of suitable formulation principles are e.g. compositions provided with an enteric coating or hydrogels of a type described by Zentner et al (U.S. Pat. No. 6,537,584) and Bae (U.S. Pat. No. 5,484,610), which hereby are incorporated by reference. Further examples of suitable formulation principles are e.g. compositions provided with a diffusion coating such as a controlled release diffusion coating, matrix particulates or matrix tablets, hydrogels, pulsed dose drug delivery systems, co-formulation with vitamin E concentrate or ethanol, TPGS, corn oil and wax etc., including any of the formulation principles mentioned above, optionally with an enteric coating.

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test according to the "half-change" method—is as follows:

within the first 3 hours after start of the test at least about 12% w/w such as, e.g., from about 12% to about 60% w/w, from about 15% to about 50% w/w, from about 20% to about 40% w/w, from about 20% to about 35% w/w, or about 25% w/w, or about 30% w/w of the total amount of the fumaric acid ester is released, and/or within the first 4 hours after start of the test at the most about 35% w/w such as, e.g., from about 15% to about 35% w/w, from about 20% to about 30% w/w, or about 25% w/w of the total amount of the fumaric acid ester is released, and/or within the first 5 hours after start of the test at the most about 45% w/w such as, e.g., from about 10% to about 45% w/w, from about 15% to about 40% w/w, from about 15% to about 35% w/w, from about 20% to about 30% w/w, or about 25% w/w, or about 30% w/w of the total amount of the fumaric acid ester is released, and/or within the first 7 hours after start of the test at the most about 65% w/w such as, e.g., from about 20% to about 65% w/w, from about 20% to about 60% w/w, from about 20% to about 50% w/w, from about 25% to about 45% w/w, from about 30% to about 45% w/w, or about 40% w/w, or about 45% w/w of the total amount of the fumaric acid ester is released, and/or within the first 8 hours after start of the test at the most about 92% w/w such as, e.g., from about 25% to about 92% w/w, from about 25% to about 90% w/w, from about 30% to about 80% w/w, from about 35% to about 70% w/w, from about 40% to about 65% w/w, from about 45% to about 60% w/w, from about 50% to about 60% w/w, or about 55% w/w, or a bout 60% w/w of the total amount of the fumaric acid ester contained in the composition is released, and/or within the first 8 hours after start of the test at the most about 60% w/w such as, e.g., from about 30% to about 60% w/w, from about 40% to about 55% w/w, or about 50% w/w of the total amount of the fumaric acid ester contained in the composition is released, and/or within the first 12 hours after start of the test at the most about 99% w/w such as, e.g., from about 30% to about 99% w/w, from about 30% to about 95% w/w, from about 35% to about 90% w/w, from about 40% to about 85% w/w, from about 45% to about 80% w/w, from about 50% to about 75% w/w, from about 55% to about 75% w/w, from about 60% to about 75% w/w, or about 65% w/w, or about 70% w/w of the total amount of the fumaric acid ester contained in the composition is released, and/or within the first 12.5 hours after start of the test at the most about 85% w/w such as, e.g., from about 50% to about 85% w/w, from about 60% to about 80% w/w, or about 75% w/w of the total amount of the fumaric acid ester contained in the composition is released, and/or within the first 18 hours after start of the test at least about 80% w/w such as, e.g., about 80% w/w or more, about 85% w/w or more, about 90% w/w or more or about 95% w/w or more of the total amount of the fumaric acid ester contained in the composition is released.

Slow Release

In the following is given a description of specific embodiments, wherein the fumaric acid ester is released in a slow or delayed manner wherein the release pattern is suitable for compositions that are administered once daily. Examples of suitable formulation principles are any of those described above.

Accordingly, in one aspect the invention relates to a controlled release pharmaceutical composition for oral use comprising as an active substance one or more fumaric acid esters selected from di-($C_1$-$C_5$)alkylesters of fumaric acid and mono-($C_1$-$C_5$)alkylesters of fumaric acid, or a pharmaceutically acceptable salt thereof, wherein the release of the fumaric acid ester—when subjected to an in vitro dissolution test employing water as dissolution medium—is as follows:

within the first 7 hours after start of the test at the most about 35% w/w such as, e.g., from about 15% to about 35% w/w, from about 20% to about 30% w/w, or about 25% w/w of the total amount of the fumaric acid ester contained in the composition is released, and/or within the first 11 hours after start of the test at the most about 60% w/w such as, e.g., from about 30% to about 60% w/w, from about 40% to about 55% w/w, or about 50% w/w of the total amount of the fumaric acid ester contained in the composition is released, and/or within the first 14 hours after start of the test at the most about 85% w/w such as, e.g., from about 50% to about 85% w/w, from about 60% to about 80% w/w, or about 75% w/w of the total amount of the fumaric acid ester contained in the composition is released, and/or within the first 18 hours after start of the test at least about 80% w/w such as, e.g., about 80% w/w or more, about 85% w/w or more, about 90% w/w or more or about 95% w/w or more of the total amount of the fumaric acid ester contained in the composition is released.

Typically, as described above, the compositions according to the invention are designed to deliver the active substance (i.e. the monoalkylester of fumaric acid, which in turn is metabolised to fumaric acid and, which subsequently is subjected to a rapid elimination process) in a prolonged manner. Apart from the characteristic in vitro release patterns described herein, such a prolonged release is reflected in the pharmacokinetic parameters obtained after a clinical study as well. Accordingly, it is contemplated that the $C_{max}$ of the monoalkylester of fumaric acid (which appears in the plasma upon hydrolysis or metabolism of the dialkylester administered) is of the same order of magnitude as previously described in the literature provided that a similar or equivalent dose is administered (i.e. $C_{max}$ of monomethylfumarate in a range of from about 0.4 to about 2.0 mg/l corresponding to an oral dose of 120 to 240 mg dimethylfumarate). However, in order to avoid many frequent daily administrations (2-4 tablets 1-3 times daily) it is an aim to prolong the time period where the concentration is within the therapeutic window. Accordingly, it is contemplated that $W_{50}$ (i.e. the time period in which the plasma concentration is 50% of $C_{max}$ or more) is prolonged compared to the marketed treatment with at least 10% such as, e.g. at least 20%, at least 30%, at least 40% or at least 50%. A suitable $W_{50}$ is believed to be at least 2 hours such as in a range of from about 2 to about 15 hours or from about 2.5 to about 10 hours or from about 3 to about 8 hours.

Furthermore, it is contemplated that a controlled release composition according to the invention may lead to a reduced interindividual and/or intraindividual variation in the plasma profile and to a reduced dependency on whether the composition is taken together with or without food (a reduced variation of the plasma concentration profile of monomethylfumarate when the pharmaceutical composition is administered with or without concomitant food intake). Therefore, the controlled release composition according to the invention may lead to a reduced frequency of dosing and/or a reduced average total daily dose, and/or an increased efficacy at the same total daily dose of the active substance compared to Fumaderm®.

Different kinetic models, such as zero-order (1), first-order (2), square-root (Higuchi's equation) (3) can be applied to the interpretation of the drug release kinetic.

$$M_t = M_0 + k_0 * t \qquad 1:$$

$$ln M_t = ln M + k_1 t \qquad 2:$$

$$M_t = M_0 + k_H * t^{1/2} \qquad 3:$$

In these equations, $M_t$ is the cumulative amount of drug released at any specified time point and $M_0$ is the dose of active substance incorporated in the pharmaceutical composition. $k_0$, $k_1$ and $k_H$ are rate constants for zero-order, first-order and Higuchi's equation, respectively.

One aspect of the invention relates to a zero-order dissolution release profile. Another aspect relates to a first-order dissolution release profile. A further aspect relates to a square-root (Higuchi's equation) dissolution release profile.

In one aspect of the invention a controlled release pharmaceutical composition comprising as an active substance from 10% to 90% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, from 2% to 40% by weight pharmaceutically acceptable polymer(s), and from 1% to 40% by weight hydrophilic excipient(s), and optionally pharmaceutically acceptable excipients or additives, is provided.

In another aspect of the invention a controlled release pharmaceutical composition comprising as an active substance from 40% to 60% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, from 15% to 25% by weight pharmaceutically acceptable polymer(s), and from 2% to 15% by weight hydrophilic excipient(s), and optionally pharmaceutically acceptable excipients or additives, is provided.

In a further aspect of the invention a controlled release pharmaceutical composition comprising as an active substance from 65% to 80% by weight of one or more fumaric acid esters selected from di-($C_1$-$C_5$)alkylesters of fumaric acid and mono-($C_1$-$C_5$)alkylesters of fumaric acid, or a pharmaceutically acceptable salt thereof, from 10% to 25% by weight pharmaceutically acceptable polymer(s), and from 2% to 15% by weight hydrophilic excipient(s), and optionally pharmaceutically acceptable excipients or additives, is provided.

Examples of "pharmaceutically acceptable polymer(s)" comprises but are not limited to ethylcellulose, or methacrylic/acrylic acid copolymers, such as ammonio methacrylate copolymer type A and B or methacrylic acid copolymer A and B.

Examples of "hydrophilic excipient(s)" comprises but are not limited to polyethylene glycol (PEG), povidone, hydroxyl propyl cellulose (HPC), hydroxyethyl starch (HES) or hydroxypropyl methyl cellulose (HPMC) or a material with similar properties, or a combination thereof.

In a further aspect of the invention a controlled release pharmaceutical composition, wherein the pharmaceutically acceptable polymer is ethyl cellulose, is provided.

In another aspect of the invention a controlled release pharmaceutical composition, wherein the hydrophilic excipient is hydroxyl propyl cellulose, is provided.

In another aspect of the invention a controlled release pharmaceutical composition, wherein the hydrophilic excipient is polyethylene glycol, is provided.

In yet another aspect of the invention a controlled release pharmaceutical composition comprising as an active substance as an active substance from 10% to 90% by weight of one or more fumaric acid esters selected from di-($C_1$-$C_5$) alkylesters of fumaric acid and mono-($C_1$-$C_5$)alkylesters of fumaric acid, or a pharmaceutically acceptable salt thereof, and 2% to 40% by weight methacrylic acid copolymer A and B in a weight ratio between 1:9 and 9:1, and optionally pharmaceutically acceptable excipients or additives, is provided.

In a further aspect of the invention a controlled release pharmaceutical composition comprising from 50% to 90% of one or more fumaric acid esters selected from di-($C_1$-$C_5$) alkylesters of fumaric acid and mono-($C_1$-$C_5$)alkylesters of fumaric acid, or a pharmaceutically acceptable salt thereof, is provided.

Various controlled release formulations, not limiting the scope of the present invention, illustrating the invention are described hereafter (all concentrations based on the final tablet):

1) Granules

Granules may be prepared by mixing and/or granulating the active substance at a concentration of about 10 to about 90%, especially from about 50 to about 70%, with granulating excipients, such as pharmaceutical acceptable polymers, e.g. ethylcellulose such as Ethocel® NF premium, or methacrylic/acrylic acid copolymers, such as ammonio methacrylate copolymer type A and B (in a weight ratio of 1:9 to 9:1) or methacrylic acid copolymer A and B (in a weight ratio of 1:9 to 9:1), incorporated at a concentration between about 2 to about 40%. Hydrophilic excipients such as polyethylene glycol (PEG), povidone, hydroxyl propyl cellulose (HPC), hydroxyethyl starch (HES) or hydroxypropyl methyl cellulose (HPMC) at a concentration of about 1 to about 40% and/or pharmaceutical acceptable surfactants with HLB values above 8 at a concentration of about 0.01 to about 3% may be incorporated.

2) Micro-Crystal Formulation

Crystallization is performed in any suitable organic solvent for re-crystallisation, such as isopropanol, at an appropriate temperature such as e.g. between +70° C. and −20° C. A hydrocolloid (e.g. HPMC) or a surfactant (e.g. polysorbate) can be used at an appropriate concentration to manipulate the growth of the crystals during recrystallization. Any granulating/coating excipient, such as pharmaceutically acceptable polymers, may be used e.g. ethylcellulose at a concentration of about 10 to about 50%, especially about 20 to about 35%, polymethacryllates such as ammonio methacrylate copolymer type A and B or methacrylic acid copolymer A and B. As a hydrophilic excipient mention can be made of e.g PEG 400.

3) Capsules and Sachets

A capsule (e.g. a capsule of gelatine, HPMC or a starch derivative) or a sachet may be filled with coated microcrystals or coated granules and if necessary appropriate amounts of filling excipients such as sugaralcoholes e.g. mannitol, and/or glidants.

4) Tablets

Tablets may be based on either micro-crystals or granules. When it comes to producing tablets in large scale, especially on a rotary machine, further excipients to increase flow ability or to improve tabletting-behaviour may be needed. As filling and binding excipients, if required, mention can be made of e.g. microcrystalline cellulose, such as Avicel® 102, and cellulose at a concentration of about 1 to about 60%, crystalline, spray dried or granulated lactose monohydrate e.g. Tablettose®, as well as anhydrous lactose monohydrate, at a concentration of about 5 to about 60%, sugar alcohols, such as sorbitol and mannitol, at a concentration of about 0 to about 40% and modified starch at a concentration of about 0 to about 40%. Furthermore disintegration agents such as starch and starch-derivates such as sodium starch glycolate (at a concentration of about 0.2 to about 10%), crospovidone (at a concentration of about 0.2 to about 10%), sodium carboxymethylcellulose (at a concentration of about 0.1 to about 10%), glidants such as colloidal anhydrous and hydrous silica (at a concentration of about 0.2 to about 4%), and lubricants, e.g. magnesium stearate, calcium behenate, and calciumarachinate (at a concentration of about 0.2 to about 3%) or sodium stearyl fumarate (at a concentration of about 1 to about 8%) can be added.

Dosage

Apart from providing compositions having different content of fumaric acid present, the invention also provides e.g. kits containing two or more containers e.g. with compositions having various amounts of the fumaric acid included. Such kits are suitable for use in those situations where an increasing dosage is required over time. A normal up-scale of the dosage is given below:

| Week | Morning | Noon | Evening | Strength |
| --- | --- | --- | --- | --- |
| 1 | 1 | — | — | A |
| 2 | 1 | — | 1 | A |
| 3 | 1 | — | 1 | B |
| 4 | 1 | — | — | B |
| 5 | 1 | — | 1 | B |
| 6 | 1 | 1 | 1 | B |
| 7 | 2 | 1 | 1 | B |
| 8 | 2 | 1 | 2 | B |
| 9 | 2 | 2 | 2 | B |

A corresponds to a low strength such as about 30 mg dimethylfumarate (or a corresponding effective dose of another fumaric acid ester)

B corresponds to a higher strength such as about 120 mg dimethylfumarate (or a corresponding effective dose of another fumaric acid ester)

In one aspect of the invention a controlled release pharmaceutical composition, wherein the amount of one or more fumaric acid esters selected from di-($C_1$-$C_5$)alkylesters of fumaric acid and mono-($C_1$-$C_5$)alkylesters of fumaric acid, or a pharmaceutically acceptable salt thereof, in a dosage form is from 90 mg to 360 mg active substance, such as 90, 120, 180, 240 or 360 mg active substance, is provided. In a further aspect of the invention the amount of active substance is 120, 180 or 240 mg active substance. In yet a further aspect of the invention, the amount of active substance is 180 or 360 mg.

The daily dosage of the controlled release pharmaceutical composition according to the invention that is administered to treat a patient depends on a number of factors among which are included, without limitation, weight and age and the underlying causes of the condition or disease to be treated, and is within the skill of a physician to determine. In one aspect of the invention the daily dosage can be e.g. from 240 to 360 mg active substance given in one to three doses, in another aspect from 360 to 480 mg active substance given in one to three doses, in another aspect 480 to 600 mg active substance given in one to three doses, in another aspect 600 to 720 mg active substance given in one to three doses, in another aspect 720 to 840 mg active substance given in one to three doses, in another aspect 840 to 960 mg active substance given in one to three doses and in yet another aspect 960 to 1080 mg active substance given in one to three doses.

In one aspect of the invention the controlled release pharmaceutical composition is in the form of a capsule.

In another aspect of the invention the controlled release pharmaceutical composition in the form of a tablet is provided, such as a tablet which has a shape that makes it easy and convenient for a patient to swallow e.g. a tablet which has a rounded or a rod-like shape without any sharp edges.

In another aspect of the invention a pharmaceutical composition in the form of a tablet designed to be divided into two or more parts, is provided.

The compositions according to the invention may be administered together with a meal or in relation to a meal such as e.g. in a time period corresponding to a range from at least about 30 minutes before a meal to about 2 hours after the meal, or the composition may be administered at any specific point(s) in time during the day.

In one embodiment, the total daily dose is given at bedtime, such as up to or about 30 minutes before bedtime, up to or about 60 minutes before bedtime, up to or about 90 minutes before bedtime, up to or about 120 minutes before bedtime or up to or about 180 minutes before bedtime.

The compositions and kits according to the invention are contemplated to be suitable to use in the treatment of one or more of the following conditions:
  a. Psoriasis
  b. Psoriatic arthritis
  c. Neurodermatitis
  d. Inflammatory bowel disease, such as
    i. Crohn's disease
    ii. Ulcerative colitis
  e. autoimmune diseases:
    i. Polyarthritis
    ii. Multiple sclerosis (MS)

iii. Juvenile-onset diabetes mellitus
iv. Hashimoto's thyroiditis
v. Grave's disease
vi. SLE (systemic lupus erythematosus)
vii. Sjögren's syndrome
viii. Pernicious anemia
ix. Chronic active (lupoid) hepatitis
x. Rheumatoid arthritis (RA)
xi. Optic neuritis Moreover, the novel composition or kit according to the invention may be used in the treatment of
1. Pain such as radicular pain, pain associated with radiculopathy, neuropathic pain or sciatica/sciatic pain
2. Organ transplantation (prevention of rejection)
3. Sarcoidosis
4. Necrobiosis lipoidica
5. Granuloma annulare Psoriasis has been proposed to potentially be associated with Crohn's disease (Najarian D J, Gottlieb A B, Connections between psoriasis and Crohn's disease. J Am Acad Dermatol. 2003 June;48(6):805-21), celiac disease (Ojetti V et al, High prevalence of celiac disease in psoriasis. Am J Gastroenterol. 2003 November;98(11):2574-5.), psychiatric or psychological disease, such as depression or a life crisis (Gupta M A, Gupta A K, Psychiatric and psychological co-morbidity in patients with dermatologic disorders: epidemiology and management. Am J Clin Dermatol. 2003;4 (12):833-42. and Mallbris L et al, Psoriasis phenotype at disease onset: clinical characterization of 400 adult cases. J Invest Dermatol. 2005 March; 124(3):499-504.), overweight, diabetes mellitus, excess consumption of alcohol/alcoholism, as well as psoriatic arthritis.

The present invention thus relates in one aspect to a method of treating psoriasis, psoriatic arthritis, neurodermatitis, inflammatory bowel disease, such as Crohn's disease and ulcerative colitis, autoimmune diseases, such as polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA) and optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare, which method comprises administering orally to a patient in need thereof, an effective dosage of a controlled release pharmaceutical composition according the invention.

The present invention relates in another aspect to the use of a controlled release pharmaceutical composition according to the invention for the preparation of a medicament for the treatment of psoriasis, psoriatic arthritis, neurodermatitis, inflammatory bowel disease, such as Crohn's disease and ulcerative colitis, autoimmune diseases, such as polyarthritis, multiple sclerosis (MS), juvenile-onset diabetes mellitus, Hashimoto's thyroiditis, Grave's disease, SLE (systemic lupus erythematosus), Sjögren's syndrome, Pernicious anemia, Chronic active (lupoid) hepatitis, Rheumatoid arthritis (RA) and optic neuritis, pain such as radicular pain, pain associated with radiculopathy, neuropathic pain or sciatica/sciatic pain, organ transplantation (prevention of rejection), sarcoidosis, necrobiosis lipoidica or granuloma annulare.

Furthermore, the invention also relates to treating an individual suffering from one of the conditions in the above-mentioned lists, more specifically psoriasis or psoriatic arthritis, with a composition or kit according to the invention, said individual further being in treatment with a) a topical anti-psoriatic drug such as 1) vitamin D or derivatives thereof (calcipotriol, calcipotriene), 2) a corticosteroid (such as e.g. betamethasone, desoximethasone, fluocinolone, momethasone, hydrocortisone aceponate, fluticasone, clobethasol, clobethasone, hydrocortisone butyrate, desonide, triamcinolone or hydrocortisone), 3) tazaroten, 4) ditranol, 5) tacrolimus (FK-506), and other calcineurin inhibitors, such as pimecrolimus or 6) any combination of 1-5 and/or b) an oral anti-psoriatic drug such as 1) an oral retinoid (such as acitretin or etretinate) combined or not combined with PUVA, 2) cyclosporine and other calcineurin inhibitors, such as ISA247, tacrolimus and pimecrolimus, 3) methotrexate, 4) hydroxyurea, 5) azathioprine, 6) sulphasalazine, 7) a fumarate derivative (such as e.g. Fumaderm® or BG-12), 8) rosiglitazone (Avandia) and other peroxisome proliferator-activated-γ (PPARγ) agonists or modulators, such as pioglitazone, farglitazar, GW1929, GW7845, MC-555, MBX-102/MBX-10, MBX-1828, MBX-2044, CLX-0921, R-483, reglitazar, naveglitazar (LY-519818/LY-818), netoglitazone (MCC-555), CS-7017, troglitazone, ciglitazone, tesaglitazar, isaglitazone, balaglitazone, muraglitazar, TAK-654, LBM642, DRF 4158, EML 4156, T-174, TY-51501, TY-12780, VDO-52 or AMG-131(T131) or any combination of 1-8 and/or c) a parenterally administered anti-psoriatic drug such as 1) alefacept (Amevive), 2) etanercept (Enbrel), 3) efalizumab (Raptiva), 4) onercept, 5) adalimumab (Humira) or any combination of 1-5 and/or d) an inhibitor of TNF-α not mentioned in the list under section c) above (e.g. CDP 870 or infliximab (Remicade)), administered via an enteral or parenteral route and/or e) tisocalicitrate and/or NCX 1022 and/or IDEC-131 and/or MEDI-507, and/or f) An NSAID or a COX or a LOX inhibitor such as e.g. a COX-2 inhibitor or a COX/5-LOX inhibitor, and/or g) an anti-diabetic or anti-obesity drug, such as biguanides such as metformin; metformin XR; a sulphonylurea such as chlorpropamide, glipizide, gliclazide, glyburide/glibenclamide or glimepiride; Glucovance (metformin+glyburide); Metaglip (glipizide+metformin); a peroxisome proliferator-activatedγ (PPARγ) agonist or modulator, such as rosiglitazone (Avandia), pioglitazone, farglitazar, GW1929, GW7845, MC-555, MBX-102/MBX-10, MBX-1828, MBX-2044, CLX-0921, R-483, reglitazar, naveglitazar (LY-519818/LY-818), netoglitazone (MCC-555), CS-7017, troglitazone, ciglitazone, tesaglitazar, isaglitazone, balaglitazone, muraglitazar, TAK-654, LBM642, DRF 4158, EML 4156, T-174, TY-51501, TY-12780, VDO-52 or AMG-131 (T131); Avandamet (rosiglitazone+metformin); Actos (pioglitazone+metformin); Avandaryl (rosiglitazone maleate+ glimepiride); a benzoimidazole such as FK-614; CS-917; TA-1095; ONO-5129; TAK-559; TAK-677/AJ-9667; a d-phenylalanine inducer such as senaglinide; c-3347; NBI-6024; ingliforib; BVT 3498; LY 929; SGLT2 inhibitors; CS 011; BIM 51077; R1438; R1439; R1440; R1498; R1499; AVE 0847; AVE 2268; AVE 5688; AVE 8134; TA-6666; AZD 6370; SSR 162369; TLK-17411; NN 2501; MK 431; KGA-2727; MK-767; CS-872; a beta-3 receptor antagonist such as N-5984; an alpha-glucosidase inhibitor such as acarbose, voglibose or miglitol; a glinitide/meglitinide analogue or carbamoylmethylbensoeic acid derivative such as mitiglinide, repaglinide or nateglinide; a DPP-IV inhibitor such as LAF 237 (vildagliptin), DPP728, P93/01, P32/98, PT-630 or saxagliptin; GLP-1 or GLP-1 analogues, such as exenatide, Exenatide-LAR, liraglutide (NN 2211), ZP 10/AVE 0010, LY 307161, betatropin, CJC-1131, GTP-010, SUN E7001 or AZM 134; pramlinitide acetate; insulin or insulin analogues, such as Humalog (insulin lispro), Humulin, Novolin, Novolog/NovoRapid (insulin aspart), Apidra (insulin glulisine), Lantus (insulin glargine), Exubera, Levemir/NN 304 (insulin detemir), AERx/NN 1998, Insuman, Pulmonary insulin or NN 344; sibutramine or other blockers of the presynaptic reuptake of serotonin and noradrenalin; orlistat and other inhibitors of GI lipases; β3-adrenergic receptor agonists; uncoupling proteins; (specific) antagonists of PPARγ (Peroxisome Proliferator-Activated Receptor γ); insulin secretagogues; rimonabant and other CB1 endocannabinoid receptor antagonists; bupropion; topiramate; leptin agonists; ciliary neurotrophic factor; peptide analogues of the human growth hormone fragment 177-191; cholecystokinin-A receptor agonists; melanocortin-3 agonists; noradrenergic drugs such as phentermine, diethylpropion, phendimetrazine or benzphetamine; or any combination of the anti-diabetic or anti-obesity drugs mentioned above, and/or h) a drug potentially useful in the treatment of substance abuse e.g. alcohol abuse such as naltrexone, acamprosate, disulphiram or Vivitrex (naltrexone long acting injection), and/or, i) a drug potentially useful in the treatment of Crohn's disease such as
  1. 5-ASA compounds such as sulfasalazine, oral 5-ASA formulations or rectal 5-ASA formulations,
  2. glucocorticosteroids such as systemic steroids (e.g. budesonide or prednisolone) or topically acting steroids (e.g. budesonide),
  3. antibiotics such as metronidazole or quinolones (e.g. ciprofloxacine, ofloxacine, norfloxacine, levofloxacine or moxifloxacine),
  4. immunosuppressives such as azathioprine, 6-mercaptopurine or methotrexate,
  5. nutritional therapies such as elemental or polymeric formulas or pre- and probiotics,
  6. biological therapies e.g. TNF-α inhibitors such as infliximab, adalimumab, CDP870, CDP571, etanercept or onercept,
  7. symptomatic agents such as anti-diarrheals or anti-spasmodics.

Examples of suitable NSAIDs are piroxicam, diclofenac, nabumetone, propionic acids including naproxen, flurbiprofen, fenoprofen, ketoprofen and ibuprofen, fenamates including mefenamic acid, paracetamol, indomethacin, sulindac, meloxicam, apazone, pyrazolones including phenylbutazone, salicylates including aspirin.

Examples of suitable COX-2 inhibitors are rofecoxib (Vioxx), valdecoxib (Bextra), celecoxib (Celebrex), etoricoxib (Arcoxia), lumiracoxib (Prexige), parecoxib (Dynastat), deracoxib (Deram), tiracoxib, meloxicam, nimesolide, (1,1-dimethylheptyl)-6a,7,10,10a-tetrahydro-I-hydroxy-6, 6dimethyl-6H-dibenzo[b,d]pyran carboxylic acid (CT-3), 2(5H)-Furanone, 5,5-dimethyl (I-methylethoxy) [4(methylsulfonyl)phenyl]-(DFP); Carprofen (RIMADYL), (Acetyloxy)-benzoic acid, 3-[(nitrooxy)methyl]phenyl ester (NCX4016), P54 (CAS Reg. No. 130996 0) 2,6-Bis(1,1-dimethylethyl) [(E)-(2-ethyl-1,1-dioxo isothiazolidinylidene)methyl]phenol (S-2474), 5(R)-Thio sulfonamide-3(2H)-benzofuranone (SVT-2016) and N-[3-(Fonnyl-amino) oxo phenoxy-4H benzopyran yl] methanesulfonamide ("T-614"); or a pharmaceutically acceptable salt thereof.

Examples of suitable COX/5-LOX inhibitors are licofelone (ML-3000 or [2,2-dimethyl-6-(4-chlorophenyl)-7-phenyl-2,3,dihydro-1H-pyrrolizine-5-yl]-acetic acid), di-tert-butylphenols, such as (E)-(5)-(3,5-di-tert-butyl-4-hy-droxybenzylidence)-2-ethyl-1,2-isothiazolidine-1,1-dioxide (S-2474), darbufelone or tebufelone and pharmacologically active metabolites as well as derivatives such as dihydro-dimethyl-benzofuran and PGV-20229, dihydro-dimethyl-benzofuran, thiophene derived compounds such as RWJ-63556, N-hydroxy-N-methyl-4-(2,3-bis-(4-methoxy-phenyl)-thiophen-5-yl)-butanamide (S19812), methoxytetrahydropyran derivatives, oxygenated xanthones such as 1,3,6,7-Tetrahydroxyxanthone (norathyriol)-pyrazole thiocarbamates, pyrazoles such as modified forms of phenidone containing compounds or the tri-flouro-benzole substituted pyrazoline derivative BW-755C, tepoxaline and derivatives and di-tert-butylpyrimidines.

It is contemplated that such combination therapy leads to an improved therapeutic response and/or an increased convenience for the individual, compared to said individual being treated without the composition or kit according to the invention.

In a further aspect, the invention relates to a method of reducing side effects associated with oral treatment of any of the conditions a-e and 1-5 listed above, in which method the active pharmaceutical ingredient for treating said condition is used in combination with one or more of the following agents:

a) an antacid such as 1) magnesium hydroxide, 2) magnesium trisilicate, 3) aluminium hydroxyde gel, 4) sodium hydrogencarbonate, 4) magaldrat or any combination of 1-5 and/or b) a histamine H-2 antagonist such as 1) cimetidine, 2) ranitidine, 3) nizatidine, 4) famotidine, 5) roxatidine, 6) lafutadine or any combination of 1-6 and/or c) a cytoprotective agent such as 1) sucralfate, 2) tripotassium dictitratobismuthate, 3) carbenoxolone, 4) prostaglandin E-2 analogues such as misoprostol, 5) ecabet, 6) cetraxate HCl, 7) teprenone, 8) troxipide, 9) dicyclomine hydrochloride, 10) sofalcon or any combination of 1-10 and/or d) a proton pump inhibitor (PPI) such as 1) omeprazole, 2) esomeprazole, 3) lansoprazole, 4) pantoprazole, 5) rabeprazole, 6) CS-526/R-105266, 7) AZD 0865, 8) soraprazan or any combination of 1-8, and/or e) an NSAID or a COX or a LOX inhibitor such as e.g. a COX-2 inhibitor or a COX/5-LOX inhibitor, and/or f) pentoxifylline, e.g. at a dose range of from 400 to 800 mg/day.

In a specific embodiment, the active substance is a fumaric acid ester containing compound. In particular, the fumaric ester containing compound is any and all of the salts contained in Fumaderm® or Fumaraat® or Panaclar® (BG-12) or described in U.S. Pat. Nos. 6,277,882, 6,355,676 or 6,509,376 or a formulation according to the present invention. The active pharmaceutical ingredient may be provided in a formulation according to the present invention, or any Fumaderm® or Fumaraat® or Panaclar® formulation or as e.g. described in U.S. Pat. Nos. 6,277,882, 6,355,676 or 6,509,376.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are described. All publications mentioned herein are incorporated herein by reference to disclose and describe the methods and/or materials in connection with which the publications are cited. It must be noted that as used herein and in the appended claims, the singular forms "a", "an", and "the" include plural referents unless the context clearly dictates otherwise. The patents and publications discussed herein are provided solely for their disclosure prior to the filing date of the present application. Nothing herein is to be construed as an admission that the present invention is not entitled to antedate such patent or publication by virtue of prior invention. Further, the dates of publication provided may be different from the actual publication dates which may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. The figures shown herein are not necessarily drawn to scale, with some components and features being exaggerated for clarity.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

EXAMPLES

Example 1

Preparation of Tablets 200 g granules are mixed with 150 g microcrystalline cellulose (e.g. Avicel® 102), 97.5 g lactose (e.g. Tablettose®), 10 g sodium carboxymethylcellulose (e.g. Ac-Di-Sol®) and 25 g starch for 30 min. Then 10 g magnesium stearate and 7.5 g amorphous silicium dioxide (e.g. Aerosil® 200) is added and the powder mixture is mixed for 5 min. This powder mixture is compressed to tablets in tabletting equipment (tablet diameter 10 mm, surface about 280-300 mm$^2$). The tablets are enteric coated in a pan-coating or in a fluid-bed coating process as described in Example 4.

Example 2

Preparation of Tablets 200 g micro-crystals are mixed with 150 g microcrystalline cellulose (e.g. Avicel® 102), 130 g lactose (e.g. Tablettose®), 10 g of sodium carboxymethylcellulose (e.g. Ac-Di-Sol®) and 25 mg starch for 30 min. Then 10 g magnesium stearate and 7.5 g of amorphous silicium dioxide is added and the powder mixture is mixed for 5 min. This powder mixture is compressed to tablets in tabletting equipment (tablet diameter 10 mm, surface about 280-300 mm$^2$). The tablets are enteric coated in a pan-coating or in a fluid-bed coating process as described in Example 4.

Example 3

Preparation of Capsules

Granules or micro-crystals are filled in HPMC capsules and these capsules are enteric coated as described in the following. In a pan coater Eudragit® L30D-55 is sprayed at drying temperatures of 60° C. to 80° C. onto the capsules in an amount of 20 mg polymeric material per mm$^2$. Pigments and talc are added in an appropriate amount.

Example 4

Enteric Coating of Tablets

In a pan coater Eudragit® L30D-55 is sprayed at drying temperatures of 60° C. to 80° C. onto the tablets in an amount of 6 mg polymeric material per mm$^2$. Pigments and talc are added in an appropriate amount.

Example 5

Preparation of Capsules 156 mg of micro-crystals, prepared as described in Example 15, is filled in a hard-gelatine-capsule size 0. The capsules are enteric coated by dipping them into a solution of 5% HPMCP (Pharmacoat HP 50®) in acetone four times each capsule-side.

Example 6

Preparation of Granules

In a granulation process 50 g dimethylfumarate (in the following DMF) is mixed with 1 g ethyl cellulose (e.g. Ethocel® NF premium) which is dissolved in 10 ml ethanol 96%, passed through a sieve 1.0 mm and dried at 50° C. to 60° C. for 30 min. These granules are manufactured to tablets and capsules using the same process as described in Examples 1 and 3.

Example 7

Preparation of Granules

In a granulation process 50 g DMF is mixed with 1 g polyvinylacetate (PVA) (e.g. Kollicoat® SR30) which is dissolved in 10 ml ethanol 96%, passed through a sieve 1.00 mm and dried at 50° C. to 60° C. for 30 min.

Example 8

Preparation of Granules

In a granulation process 50 g DMF is mixed with 15 g of powdered Eudragit® RL 100. After adding an appropriate amount of 2-propanol and passing through a 1.00 mm sieve, the granules are dried at 60° C. These granules are manufactured to tablets and capsules using the same process as described in Examples 1 and 3.

Example 9

Preparation of Coated Granules

In a granulation process 50 g DMF is directly mixed with 5 g Eudragit® RL30D, passed through a sieve (1.00 mm) and dried at 80° C. After sieving the granules are coated in a fluid-bed coater (Mini-Glatt) with 15 g of a 1:1 mixture Eudragit® RL30D/RS30D. The coated granules can be manufactured to tablets and capsules using the same process as described in Examples 1 and 3.

Example 10

Preparation of Coated Granules

In a granulation process 50 g DMF is mixed with 20% ethyl cellulose (e.g. Ethocel® NF premium) which is dissolved in an appropriate amount of ethanol 96%. 15% polyethylene glycole 6000 are added to the granulation liquid. The mixture is passed through a sieve 1.00 mm and dried at 50° to 60° C. for 30 min. After sieving the granules are coated in a fluid-bed coated (Mini-Glatt) with a 2:1 mixture of ethyl cellulose and polyethylene glycole 6000 in an amount of 20 mg per mm$^2$ granules surface area. These granules can be manufactured to tablets or capsules using the processes described in Examples 1 and 3.

Example 11

Preparation of Coated Granules

In a granulation process 50 g DMF is mixed with 10% ethyl cellulose (e.g. Ethocel® NF premium) which is dissolved in an appropriate amount of ethanol 96%. 6% povidone (e.g. Kollidon® 25) is added to the granulation liquid. The mixture is passed through a sieve 1.00 mm and dried at 50° to 60° C. for 30 min. After sieving the granules are coated in a fluid-bed coated (Mini-Glatt) with a 3:2 mixture of ethyl cellulose and povidone in an amount of 20 mg per mm$^2$ granule surface area.

These granules can be manufactured to tablets or capsules using the processes described in Examples 1 and 3.

Example 12

Preparation of Coated Granules

In a granulation process 50 g DMF is mixed with 10% ethyl cellulose (e.g. Ethocel® NF premium) which is dissolved in an appropriate amount of ethanol 96%. 5% hydroxypropyl cellulose (HPC) (e.g. Klucel®) are added to the granulation liquid. The mixture is passed through a sieve 1.00 mm and dried at 50° to 60° C. for 30 min. After sieving, the granules are coated in a fluid-bed coater (mini-Glatt) with a 2:1 mixture of ethyl cellulose and HPC in an amount of 20 mg per mm$^2$ granule surface area.

These granules can be manufactured to tablets or capsules using the processes described in Examples 1 and 3.

Example 13

Preparation of Coated Granules

In a granulation process 50 g DMF is directly mixed with an appropriate amount of an aqueous dispersion of Eudragit® NE30D, passed through a sieve (1.00 mm) and dried at 80° C. After sieving the granules are coated in a fluid-bed coater (Mini-Glatt) with 15 g of a 1:1 mixture Eudragit® RL30D/RS30D. The coated granules can be manufactured to tablets and capsules using the processes described in Examples 1 and 3.

Example 14

Preparation of Coated Granules

In a granulation process 50 g DMF is directly mixed with an appropriate amount of an aqueous dispersion of Eudragit® RL30D, passed through a sieve (1.00 mm) and dried at 80° C. After sieving, the granules are coated in a fluid-bed coater (Mini-Glatt) with Eudragit® NE30D. The coated granules can be manufactured to tablets and capsules using the processes described in Examples 1 and 3.

Example 15

Preparation of Coated Micro-Crystals

A saturated solution of 50 g DMF in 300 ml 2-propanol is prepared at 60° C. and slowly cooled under permanent stirring. The precipitated crystals are filtered off and dried at 50° C. The crystals are sieved and the 315-710 µm fraction is used for a coating process in either a pan coater or a fluid-bed coater (Mini-Glatt). A coating solution of 12 g ethyl cellulose (e.g. Ethocel® NF premium) and 3 g polyethylene glycole 400 in 500 g ethanol is sprayed at 60° C. onto the powder surface. After drying, the coated crystals are sieved through a 1.00 mm sieve. These coated DMF crystals can be manufactured to tablets and capsules using the processes described in Examples 2 and 3.

Example 16

Preparation of Tablets

In a granulation process 50 g DMF is mixed with 12 g Ethylcellulose (e.g. Ethocel® NF premium) and 3 g Polyethylenglycole 400 which is dissolved in 150 ml Ethanol 96%, passed through a 1.0 mm sieve, dried at 50° to 60° C. over 30 min and again passed through a sieve 1.0 mm. A placebo granulate is prepared as follows: Tablettose® and Avicel® 102 are mixed in equal shares and granulated with 2% povidone (e.g. Kollidon® 25) dissolved in water (q.s.), passed through a 1.0 mm sieve, dried at 50° to 60° C. over 30 min and again passed through a 1.0 mm sieve. 60 parts of the DMF-granulate and 38 parts of the placebo-granulate are mixed for 30 minutes in a Turbula Shaker Mixer. One part Aerosil® 200 and one part magnesium stearate are added and the blend is mixed again for 5 minutes. The blend is compressed to tablets with a diameter of 10 mm, a weight of about 260 mg and a hardness of about 50 N. The tablets are enteric coated using the processes described in Example 4.

Example 17

Preparation of Tablets

In a granulation process 50 g DMF is mixed with 12 g Ethylcellulose (e.g. Ethocel® NF premium) and 3 g Polyethylenglycole 400 which is dissolved in 150 ml Ethanol 96%, passed through a 1.0 mm sieve, dried at 50° to 60° C. over 30 min and again passed through a sieve 1.0 mm. A placebo granulate is prepared as follows: Tablettose® and Avicel® 102 are mixed in equal shares and granulated with 2% povidone (e.g. Kollidon® 25) dissolved in water (q.s.), passed through a 1.0 mm sieve, dried at 50° to 60° C. over 30 min and again passed through a 1.0 mm sieve. 60 parts of the DMF-granulate and 37 parts of the placebo-granulate are mixed for 30 minutes in a Turbula Shaker Mixer. One part carboxymethylcellulose (e.g. Ac-Di-Sol®), one part Aerosil® 200 and one part magnesium stearate are added and the blend is mixed again for 5 minutes.

The blend is compressed to tablets with a diameter of 10 mm, a weight of about 260 mg and a hardness of about 50 N. The tablets are enteric coated using the processes described in Example 4.

Example 18

Preparation of Coated Micro-Crystals

A saturated solution of 50 g DMF in 300 ml 2-propanol is prepared at 60° C. and slowly cooled under permanent stirring. The precipitated crystals are filtered off and dried at 50° C. The crystals are sieved and the 315-710 µm fraction is used for a coating process in either a pan coater or a fluid-bed coater (Mini-Glatt). A coating solution of 12 g ethyl cellulose (e.g. Ethocel® NF premium) and 3 g povidone (PVP) in 500 g ethanol is sprayed at 60° C. onto the surface of the crystals. After drying the coated crystals are sieved through a 1.00 mm sieve.

The coated DMF crystals can be manufactured to tablets and capsules using the processes described in Example 2 and 3.

Example 19

Preparation of Coated Micro-Crystals

A saturated solution of 50 g DMF in 300 ml 2-propanol is prepared at 60° C. and slowly cooled under permanent stirring. The precipitated crystals are filtered off and dried at 50° C. The crystals are sieved and the 315-710 µm fraction is used for a coating process in either a pan coater or a fluid-bed coater (Mini-Glatt). A coating solution of 12 g ethyl cellulose (e.g. Ethocel® NF premium) and 3 g hydroxylpropylcellulose (HPC) in 500 g ethanol is sprayed at 60° C. onto the powder surface. After drying the coated crystals are sieved through a 1.00 mm sieve. These coated DMF crystals can be manufactured to tablets and capsules using the processes described in Examples 2 and 3.

Example 20

Preparation of Micro-Crystals

DMF-crystals are prepared as described in Example 15, but 2% of ethyl cellulose, related to the mass of the crystals, is added directly to the 2-propanol before precipitation of the crystals.

Example 21

Preparation of Coated Micro-Crystals 50 g DMF crystals prepared as described in Example 15 are coated in a fluid-bed coater (Mini-Glatt) at a temperature of 80° C. with 20 g of an aqueous dispersion of a 1:1 mixture of Eudragit® RL30D/RS30D. These coated DMF crystals are manufactured to tablets and capsules using the processes described in Examples 2 and 3.

Example 22

Preparation of Tablets

DMF crystals prepared as described in Example 15 are directly mixed with 25% solid Eudragit® RS PO/RL PO in a ratio of 1:2 and manufactured to tablets as described in Example 2.

Example 23

Preparation of Coated Micro-Crystals

DMF crystals prepared as described in Example 15 are coated in a fluid-bed coater (Mini-Glatt) with an amount of 5% (related to the mass of the crystals) aqueous dispersion of polyvinyl acetate (e.g. Kollicoat® SR 30D). These coated DMF crystals can be manufactured to tablets and capsules using the processes described in Examples 2 and 3.

Example 24

Preparation of Granules

In a granulation process, 50 g DMF is mixed with 15% ethyl cellulose (e.g. Ethocel® NF premium) which is dissolved in an appropriate amount of ethanol 96%. 10% polyethylene glycole 6000 is added to the granulation liquid. The mixture is passed through a sieve 1.00 mm and dried at 50° to 60° C. for 30 min. These granules can be manufactured to tablets or capsules using the processes described in Examples 1 and 3.

Example 25

Preparation of Granules

In a granulation process, 50 g diethylfumarate (DEF) is mixed with 15% ethyl cellulose (e.g. Ethocel® NF premium) which is dissolved in an appropriate amount of ethanol 96%. 10% polyethylene glycole 6000 is added to the granulation liquid. The mixture is passed through a sieve 1.00 mm and dried at 50° to 60° C. for 30 min. These granules can be manufactured to tablets or capsules using the processes described in Examples 1 and 3.

Example 26

Preparation of Tablets

A granulate is prepared as described in Example 24 but instead of PEG 6000, 10% of povidone (e.g. Kollidon® 25) is added. This mixture can be manufactured to tablets or capsules using the processes described in Examples 1 and 3.

Example 27

Preparation of Tablets

A granulate is prepared as described in Example 24 but instead of PEG 6000, 10% hydroxyl propyl methylcellulose is added. This mixture can be manufactured to tablets or capsules using the processes described in Examples 1 and 3.

Example 28

50 g DMF crystals prepared as described in Example 15 are coated in a fluid-bed coater (Mini-Glatt) at a temperature of 80° C. with 20 g of an aqueous dispersion of a 1:1 mixture of Eudragit® RL30D/RS30D. The coated crystals are enteric coated in a pan coater as described in the following. Eudragit® L30D-55 are sprayed at drying temperatures of 60° C. to 80° C. onto the coated crystals in an amount of 6 mg polymeric material per $mm^2$ These double coated DMF crystals are either filled into hard gelatine or soft gelatine capsules or manufactured to tablets using the process described in Example 2.

Example 29

Preparation of Tablets

In a granulation process 50 g DMF is mixed with 12 g Ethylcellulose (e.g. Ethocel® NF premium) and 3 g hydroxypropyl cellulose (e.g. Klucel®) which is dissolved in 150 ml Ethanol 96%, passed through a sieve 1.0 mm, dried at 50° to 60° C. over 30 min and again passed through a sieve 1.0 mm.

Tablettose® and Avicel® 102 are mixed in equal shares and granulated with 2% povidone (Kollidon® 25) dissolved in water (q.s.). 60 parts of the DMF-granulate and 38 parts of the placebo-granulate are mixed for 30 minutes in a Turbula Shaker Mixer. One part Aerosil® 200 and one part magnesium stearate are added and the blend is mixed again for 5 minutes. The blend is compressed to tablets with a diameter of 10 mm, a weight of about 260 mg and a hardness of about 50 N. The tablets are enteric coated using the process described in Example 4.

Example 30

Determination of pH Controlled Release Dissolution Profile of Capsules

The dissolution profile is determined as described in the United States Pharmacopoeia using a rotating basket with 6 so called Levy-glasses with a capacity of 1 liter and 6 basket stirring elements powered by an electric motor (at 100 rpm). The Levy-glasses are filled with 0,1N HCl (the water bath has a temperature of 37° C.+/−0.5° C.) and the capsules are applied to the baskets. After 2 hours, the acid is removed from the vessels and replaced with dissolution medium (USP phosphate buffer, pH 6.5) and tested for another 6 hours. Samples (5 ml) are taken after 0, 60 and 120 minutes from the acid medium, and after 30, 60, 90, 120, 180, 240, 300 and 360 minutes from the buffer medium after replacing the dissolution medium with USP buffer. Instead of replacing the amount of drawn buffer solution after each sample, the loss of buffer is taken into account when calculating the amount of released DMF. The amount of DMF is determined by HPLC (Kontron XXX) using a Merck LiChroCART RP8 5 µM, 20 cm column, tempered at 25° C. The mobile phase consists of a mixture (35:65) of acetonitrile and 0.0725 mol/1 $NaH_2PO_4*H_2O$-buffer adjusted to pH 3.2 with phosphoric acid. The UV detector is set at a wavelength of 230 nm and a flow rate of 1.0 ml per minute. The DMF peak is detectable after a retention time of about 5 min.

Example 31

Determination of pH Controlled Release Dissolution Profile of Non-Enteric Coated Tablets The dissolution profile is determined using 6 so called Levy-glasses with a capacity of 1 liter and 6 paddles as stirring elements powered by an electric motor. The rotating speed of the paddles is 100 rpm. The Levy-glasses are filled with USP phosphate buffer, pH 6.5 (the water bath has a temperature of 37° C.+/−0.5° C.) and the tables are into the Levy-glasses. Samples (5 ml) are taken after 0, 30, 60, 90, 120, 180, 240, 300 and 360 minutes from the buffer medium after replacing the dissolution medium with USP buffer. Instead of replacing the amount of drawn buffer solution after each sample, the loss of buffer is taken into account when calculating the amount of released DMF. The amount of DMF is determined by HPLC (Kontron XXX) using a Merck LiChroCART RP8 5 µM, 20 cm column, tempered at 25° C. The mobile phase consists of a mixture (35:65) of acetonitrile and 0.0725 mol/1 $NaH_2PO_4*H_2O$-buffer adjusted to pH 3.2 with phosphoric acid. The UV detector is set at a wavelength of 230 nm and a flow rate of 1.0 ml per minute. The DMF peak is detectable after a retention time of about 5 min.

Example 32

The dissolution profile of capsules prepared as described in Example 5 is determined as described in Example 30. The dissolution profile is shown in FIG. 1.

Example 33

Figure 2:
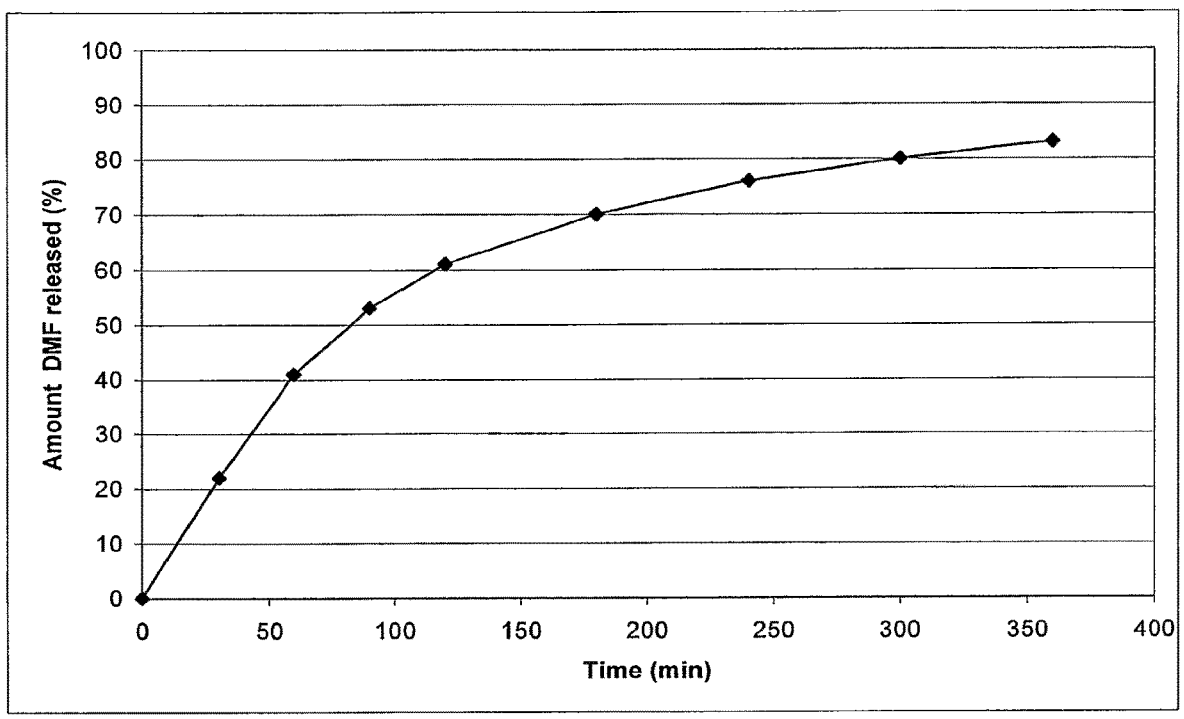
FIG. 2 shows an example of an in vitro dissolution profile of a sample of a tablet (before the enteric coating is applied) prepared as described in example 16.

The dissolution profile of the tablets (before the enteric coating is applied) prepared as described in example 16 is determined as described in Example 31. The dissolution profile is shown in FIG. 2.

Example 34

Figure 3:
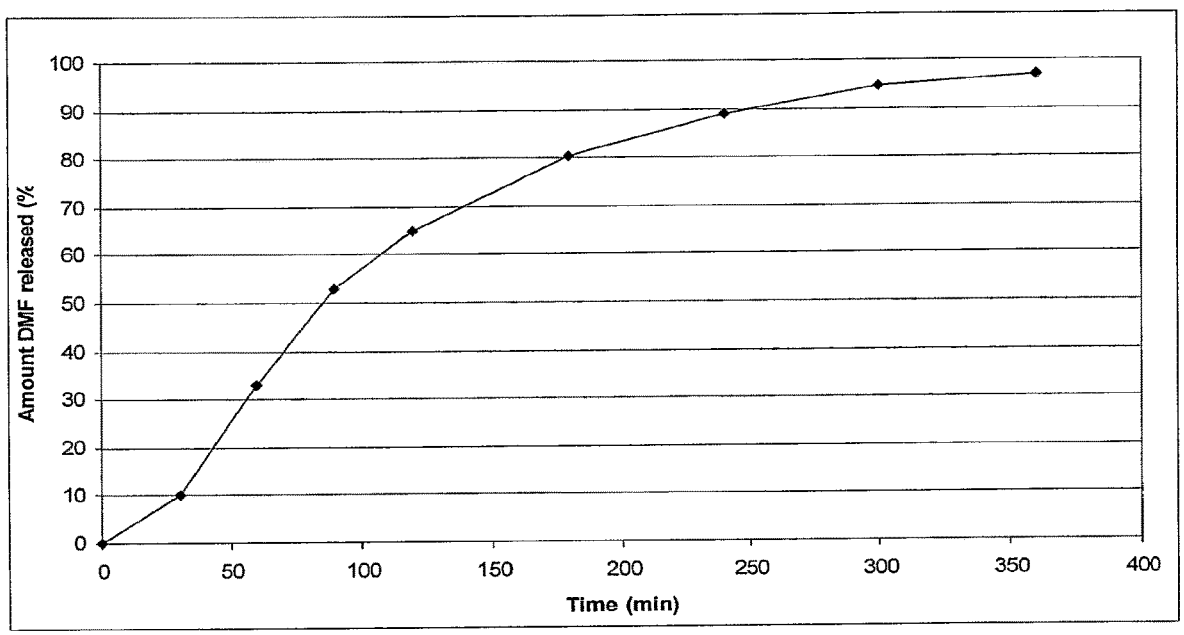
FIG. 3 shows an example of an in vitro dissolution profile of a sample of a tablet (before the enteric coating is applied) prepared as described in example 17.

The dissolution profile of the tablets (before the enteric coating is applied) prepared as described in example 17 is determined as described in Example 31. The dissolution profile is shown in FIG. 3.

The invention claimed is:

1. An oral pharmaceutical composition comprising (i) dimethylfumarate as the only fumaric acid ester active substance, (ii) one or more enteric coating polymers, and (iii) one or more pharmaceutically acceptable excipients, said composition being capable of providing controlled release in vivo in humans, wherein said dimethylfumarate is present in an amount of 50-90%, by weight, of said composition, and the release of said dimethylfumarate, when subjected to an in vitro dissolution test employing 0.1N hydrochloric acid as dissolution medium during the first 2 hours of the test and then 0.05 M phosphate buffer pH 6.5 as dissolution medium, is as follows: within the first 3 hours after the start of the test at the most 35% by weight of the total amount of the dimethylfumarate is released.

2. The composition of claim 1, wherein said composition is in a tablet form.

3. The composition of claim 1, wherein said composition is contained in a capsule.

4. The composition of claim 3, wherein said composition is in the form of pellets or beads.

5. The composition of claim 3, wherein said composition is in the form of granules.

6. The composition of claim 3, wherein said composition is in the form of micro-crystals.

7. The composition of claim 1, wherein said one or more enteric coating polymers comprises a polyacrylamide, a phthalate derivative, an acid phthalate of a carbohydrate, amylose acetate phthalate, cellulose acetate phthalate, a cellulose ester phthalate, a cellulose ether phthalate, hydroxypropylcellulose phthalate, hydroxypropylethylcellulose phthalate, hydroxypropylmethlycellulose phthalate, methylcellulose phthalate, polyvinyl acetate phthalate, a poly acrylic methacrylic acid copolymer, shellac, or a vinyl acetate and crotonic acid copolymer.

8. The composition of claim 7, wherein said one or more enteric coating polymers is a poly acrylic methacrylic acid copolymer.

* * * * *